US009585755B2

(12) United States Patent
Rose et al.

(10) Patent No.: US 9,585,755 B2
(45) Date of Patent: Mar. 7, 2017

(54) FRACTURE FIXATION SYSTEMS HAVING INTRAMEDULLARY SUPPORT

(71) Applicant: Smith & Nephew, Inc., Memphis, TN (US)

(72) Inventors: John Rose, Collierville, TN (US); James K. Rains, Cordova, TN (US); William D. Patterson, Southaven, MS (US); Mark T. Lewis, Memphis, TN (US); Gene E. Austin, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/723,351

(22) Filed: May 27, 2015

(65) Prior Publication Data
US 2015/0250593 A1   Sep. 10, 2015

Related U.S. Application Data

(62) Division of application No. 14/008,456, filed as application No. PCT/US2012/030947 on Mar. 28, 2012, now Pat. No. 9,060,823.

(60) Provisional application No. 61/468,991, filed on Mar. 29, 2011.

(51) Int. Cl.
*A61F 2/28* (2006.01)
*A61L 27/56* (2006.01)
*A61L 27/58* (2006.01)
*A61B 17/82* (2006.01)
*A61F 2/00* (2006.01)

(52) U.S. Cl.
CPC ............ *A61F 2/2846* (2013.01); *A61B 17/82* (2013.01); *A61F 2/0077* (2013.01); *A61L 27/56* (2013.01); *A61L 27/58* (2013.01); *A61F 2002/0086* (2013.01); *A61F 2002/285* (2013.01); *A61F 2002/2835* (2013.01); *A61F 2002/2839* (2013.01); *A61L 2430/02* (2013.01)

(58) Field of Classification Search
None
See application file for complete search history.

(56) References Cited

FOREIGN PATENT DOCUMENTS

CN              101391116 A     *  3/2009

OTHER PUBLICATIONS

Chinese Office Action; Chinese Patent Office; Chinese Patent Application No. 201280026342.X; Apr. 1, 2016; 8 pages.
(Continued)

*Primary Examiner* — Sameh Boles
(74) *Attorney, Agent, or Firm* — Taft Stettinius & Hollister LLP

(57) ABSTRACT

Orthopedic fracture repair implants, systems and methods are disclosed. Implants include one or more of biocompatible sleeves and struts. The implants, systems and methods are applied to bone fractures, such as segmentation fractures.

30 Claims, 34 Drawing Sheets

(56) References Cited

OTHER PUBLICATIONS

Australian Patent Office, Patent Examination Report No. 1, dated Jan. 6, 2016, 5 pages.
European Patent Office, Communication Pursuant to Article 94(3) EPC, dated Feb. 16, 2016, 4 pages.
European Examination Report; European Patent Office; European Patent Application No. 12764359.1; Oct. 10, 2016; 4 pages.
Chinese Office Action; Chinese Patent Office; Chinese Patent Application No. 201280026342.X; Aug. 22, 2016; 10 pages.
Australian Examination Report; Australian Patent Office; Australian Patent Application No. 2012236602; Dec. 12, 2016; 3 pages.

* cited by examiner

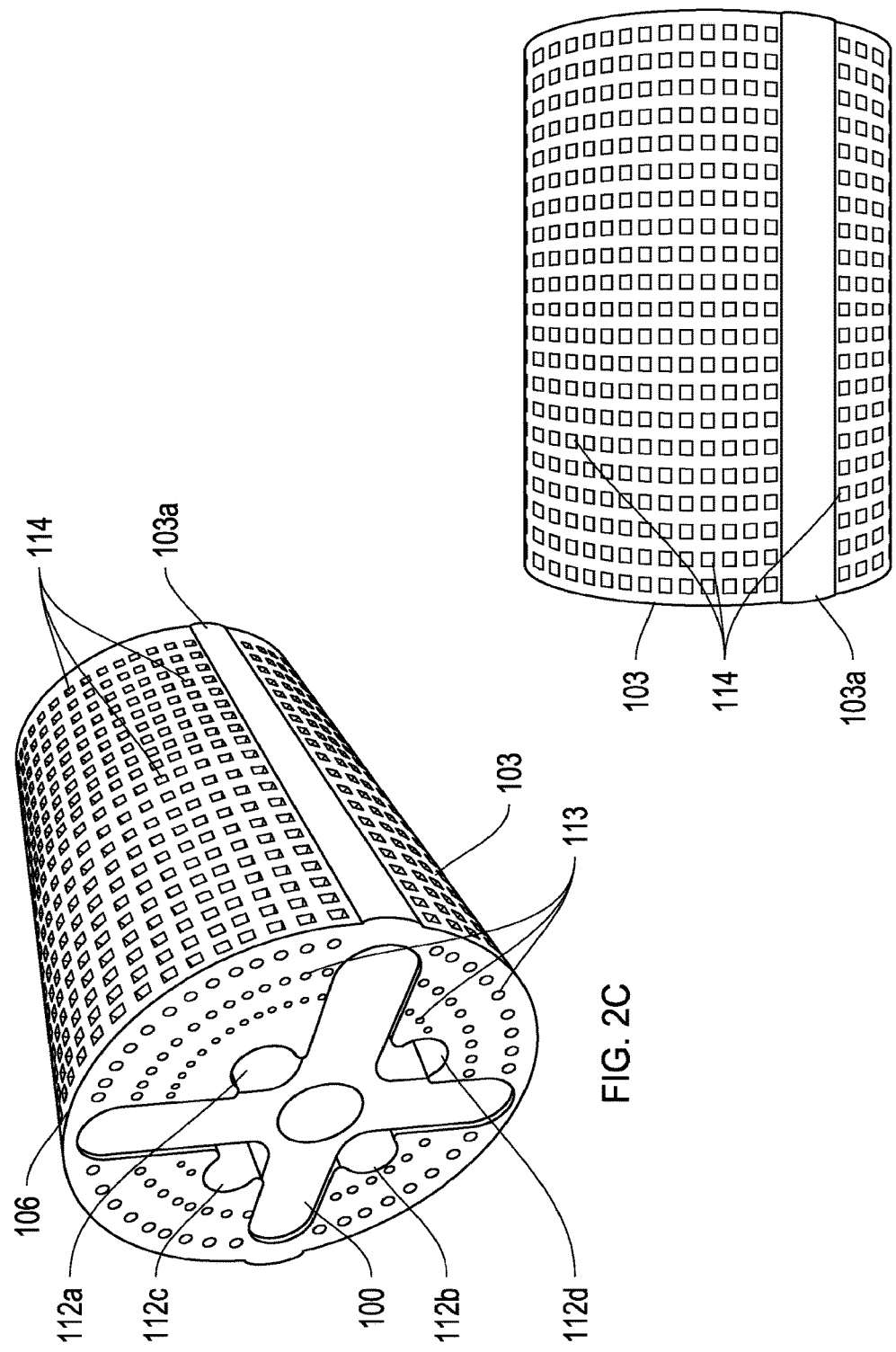

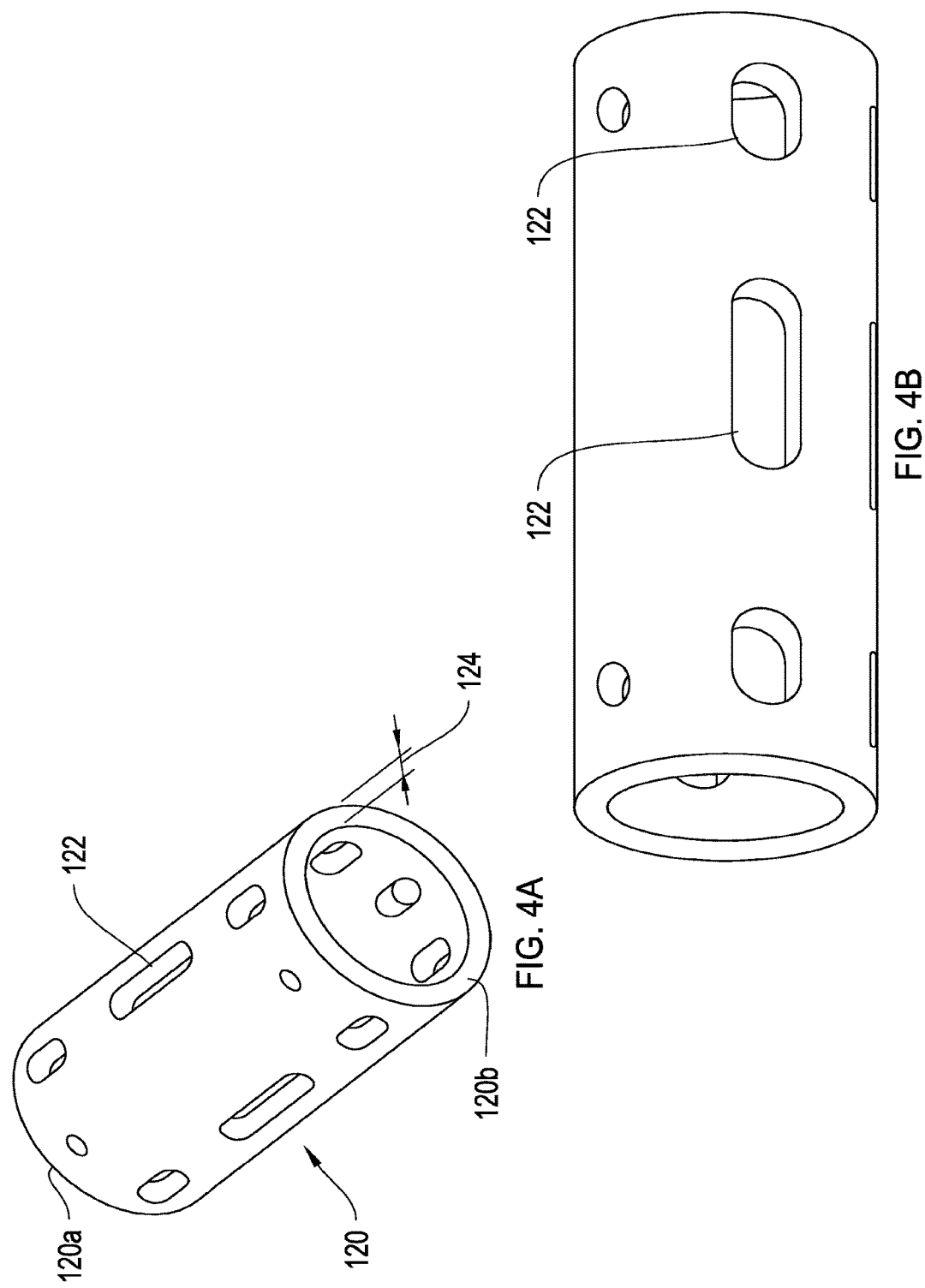

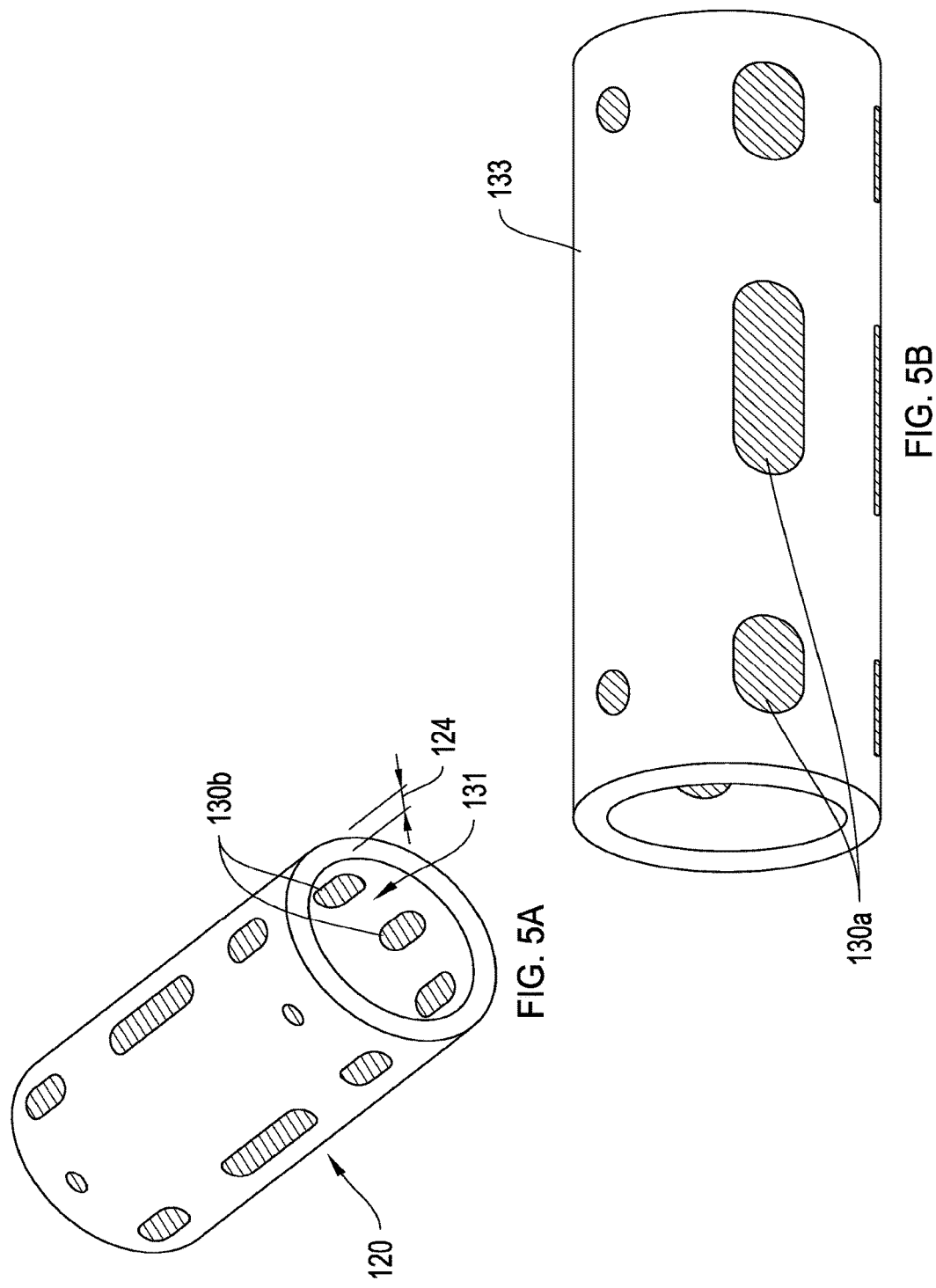

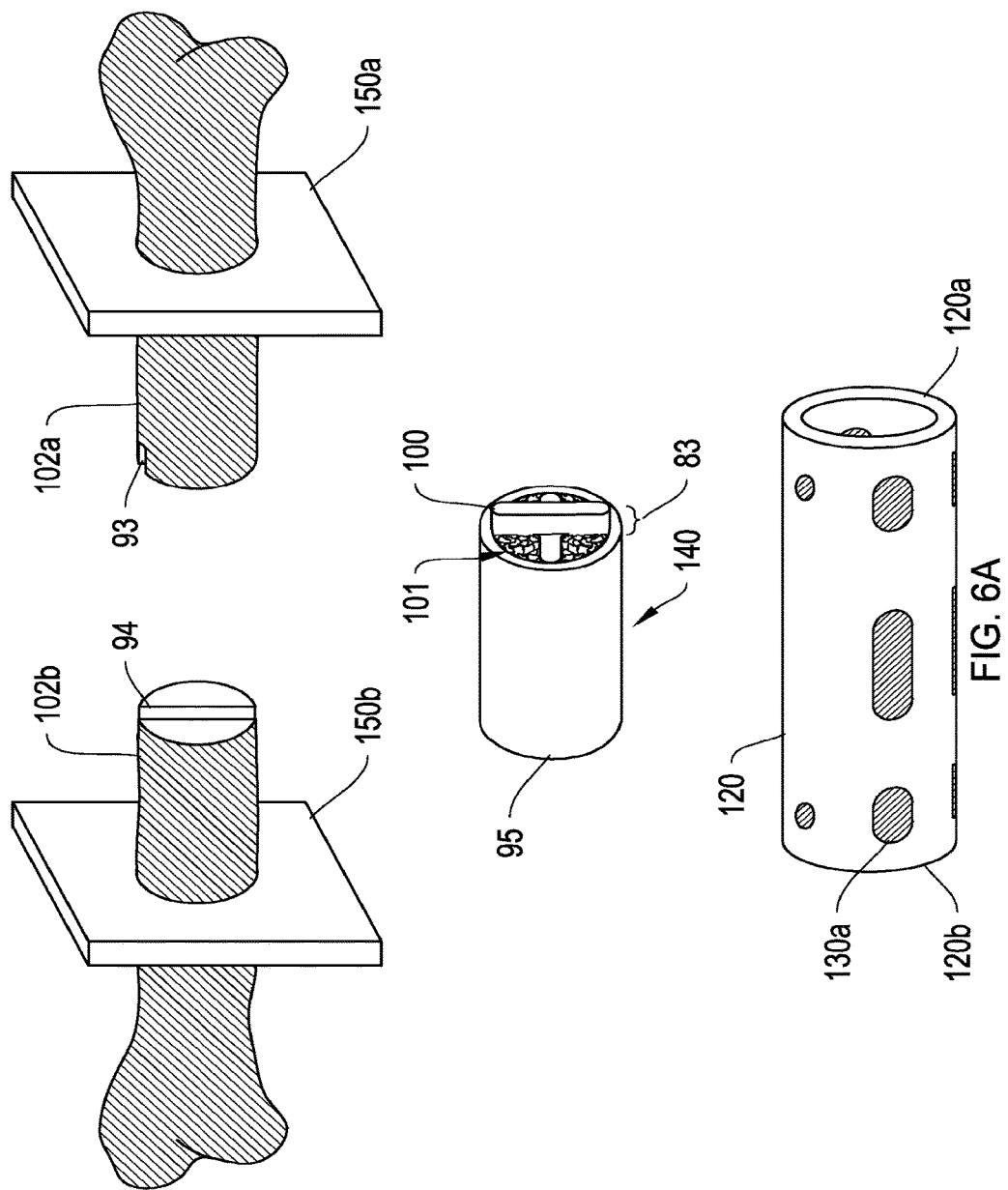

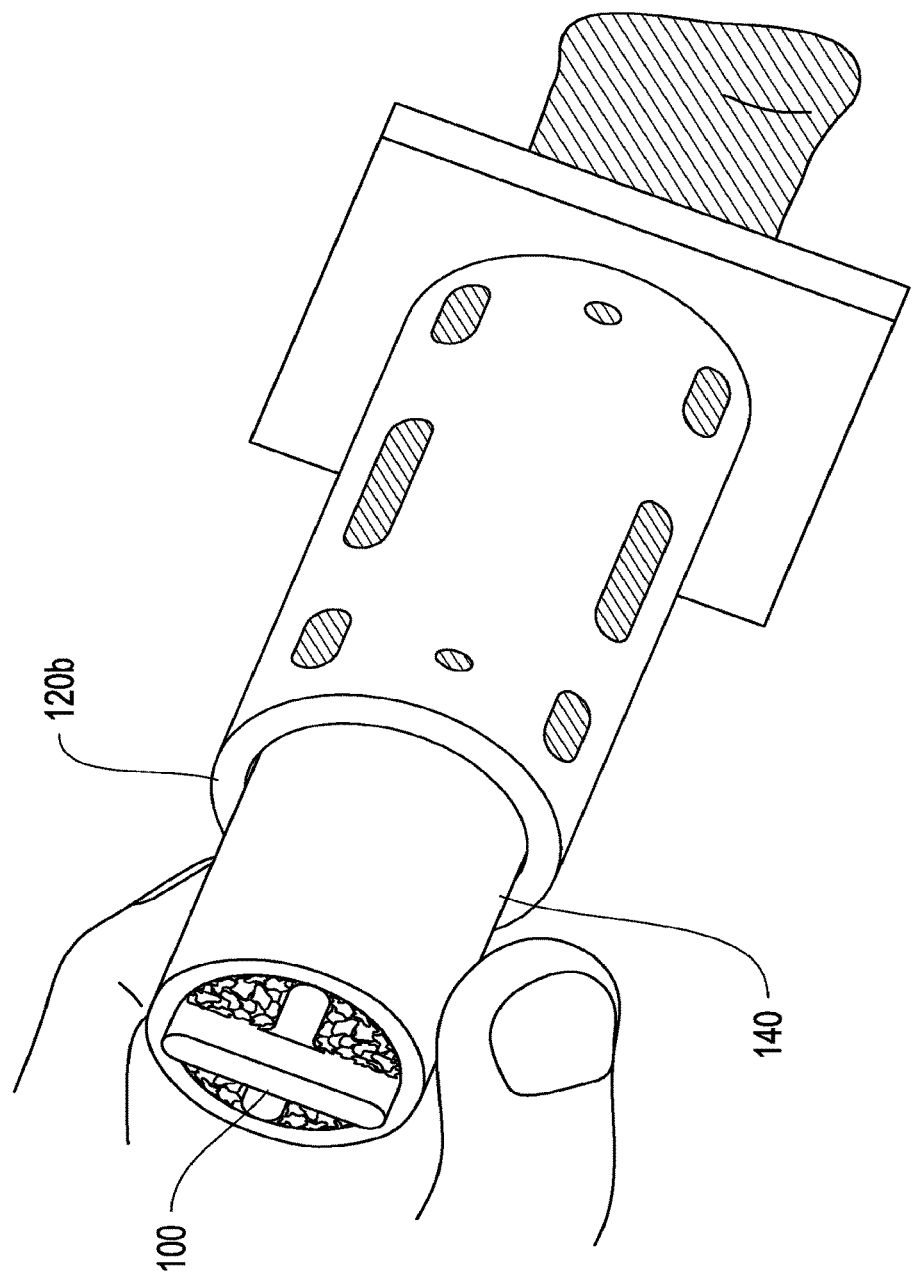

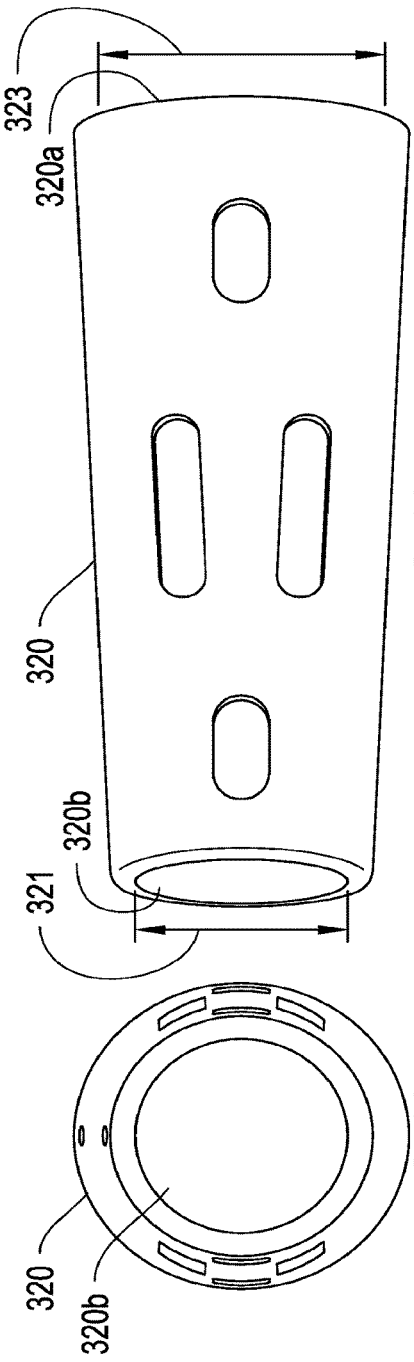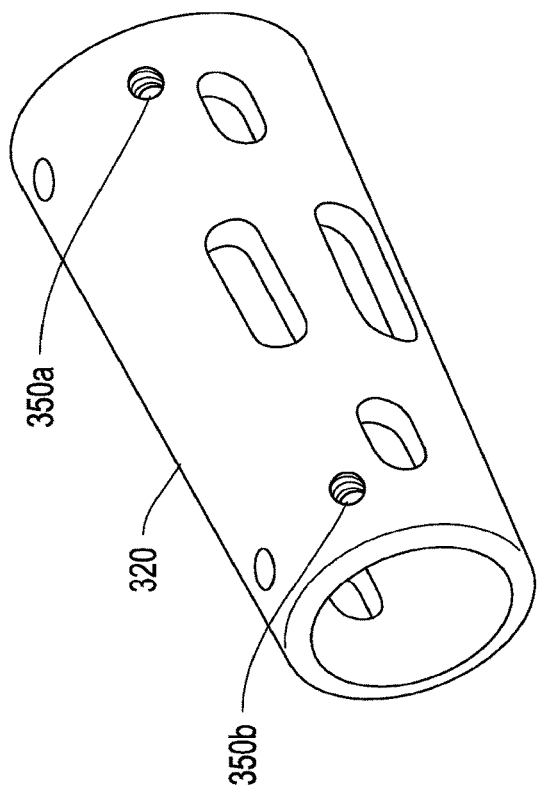
FIG. 11A
FIG. 11B
FIG. 11C

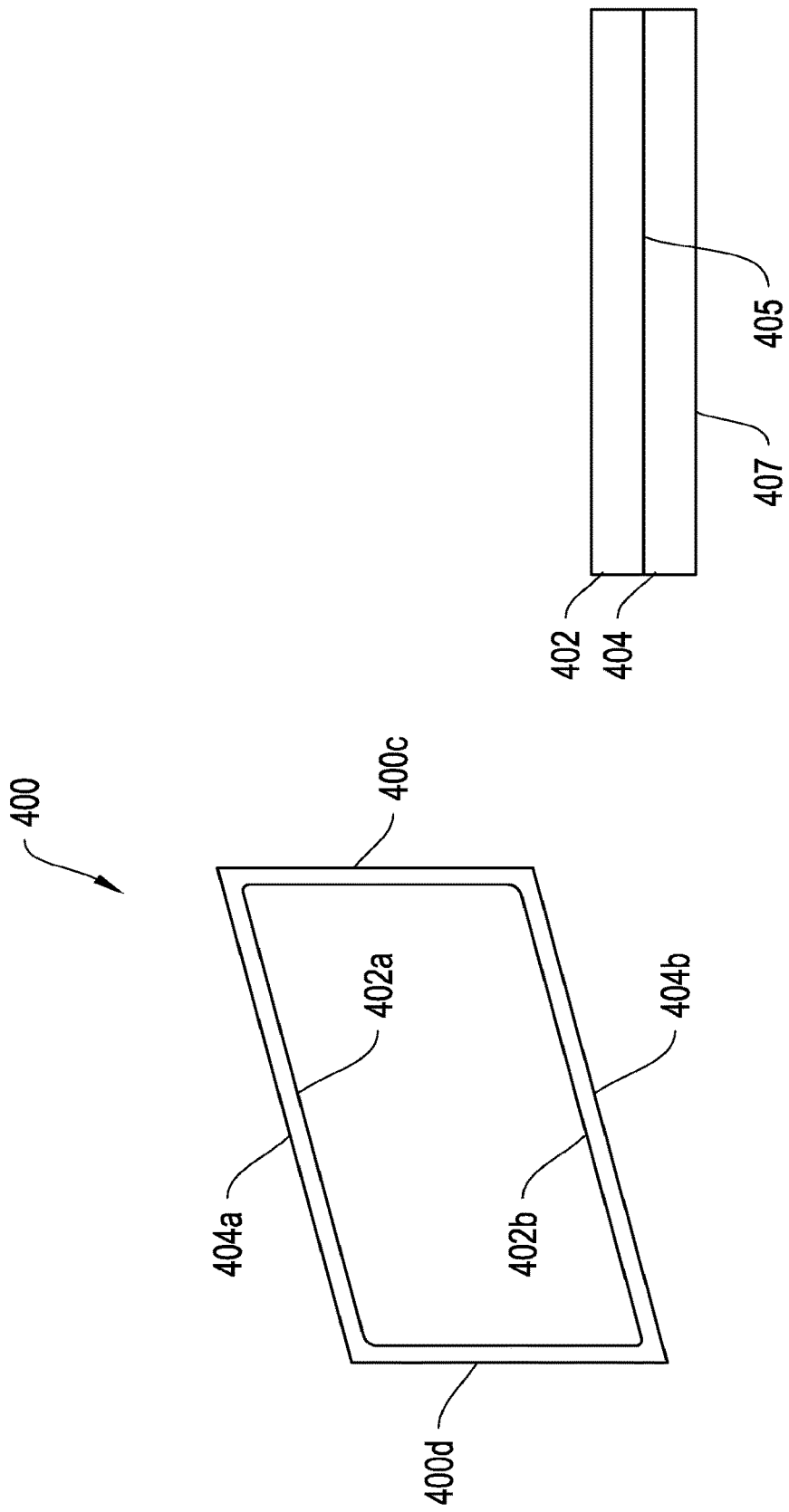

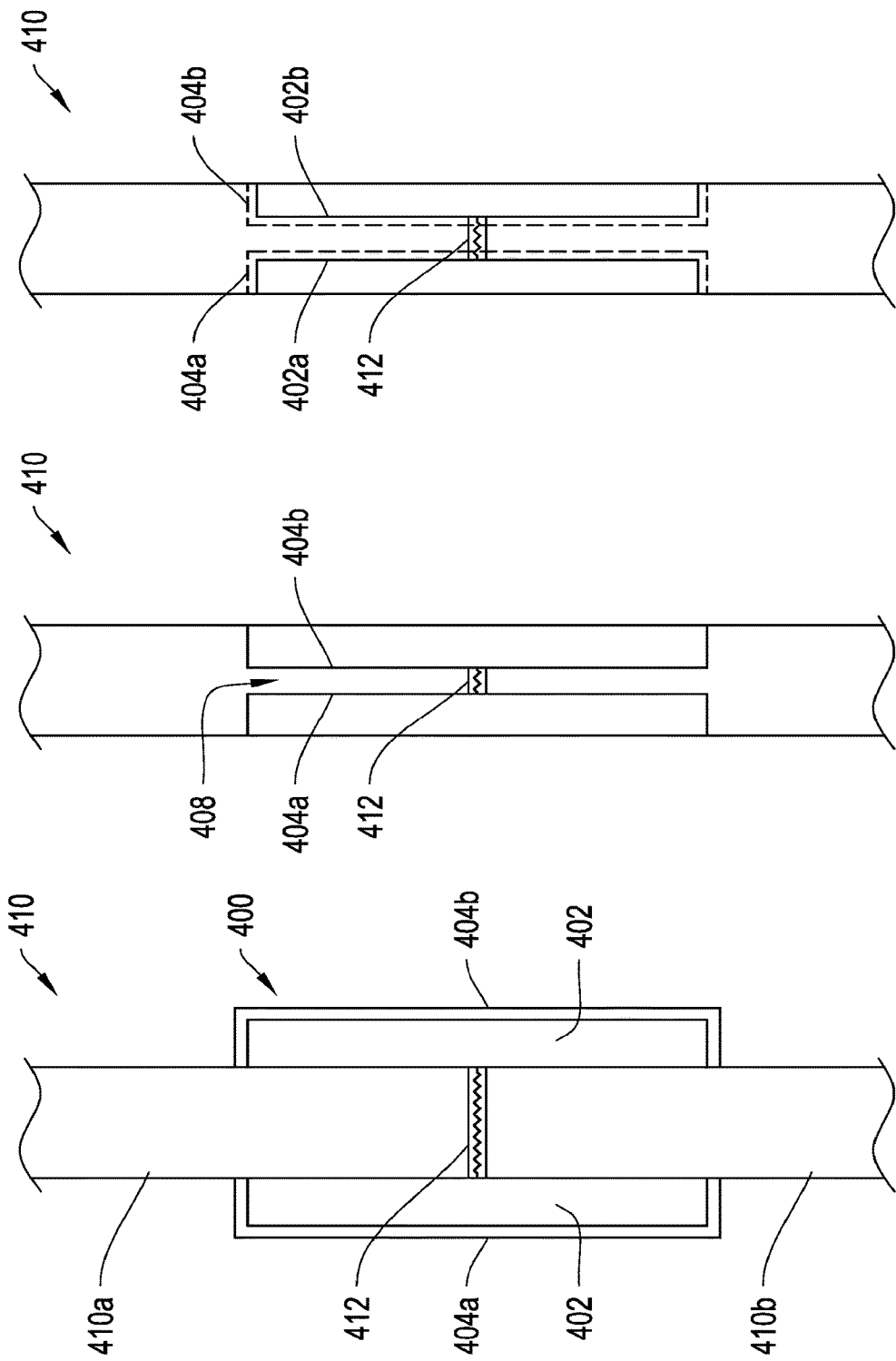

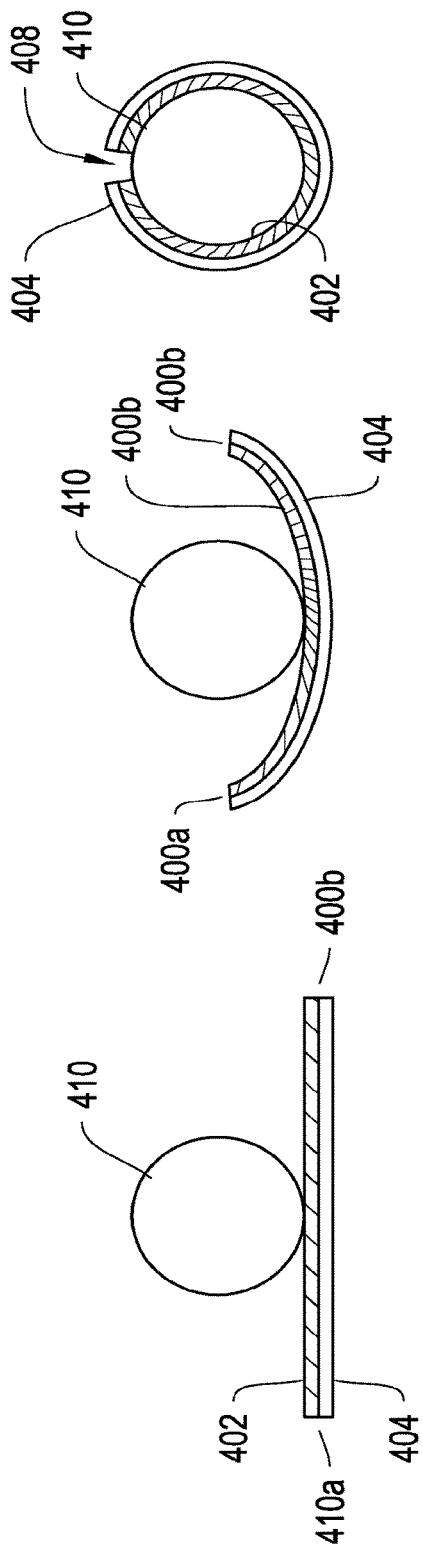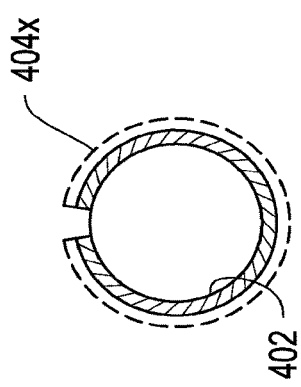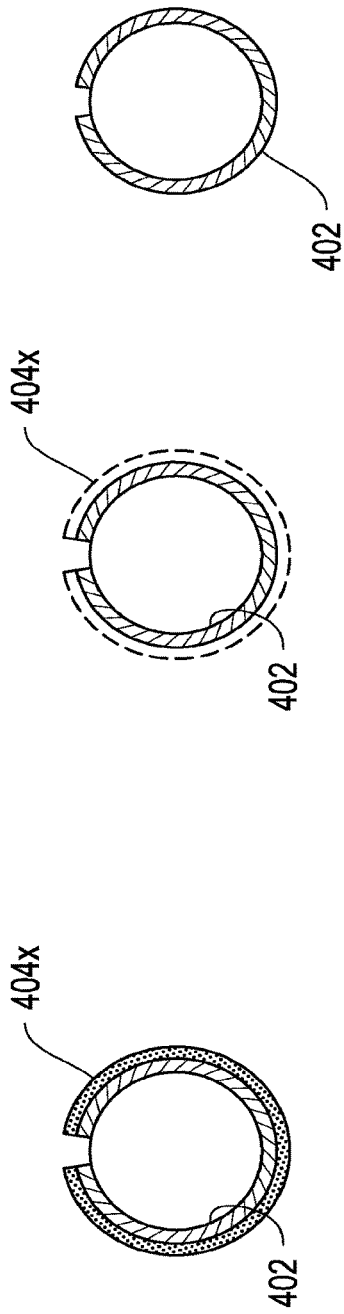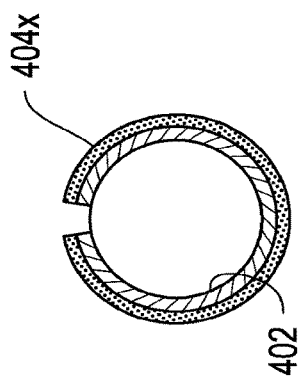

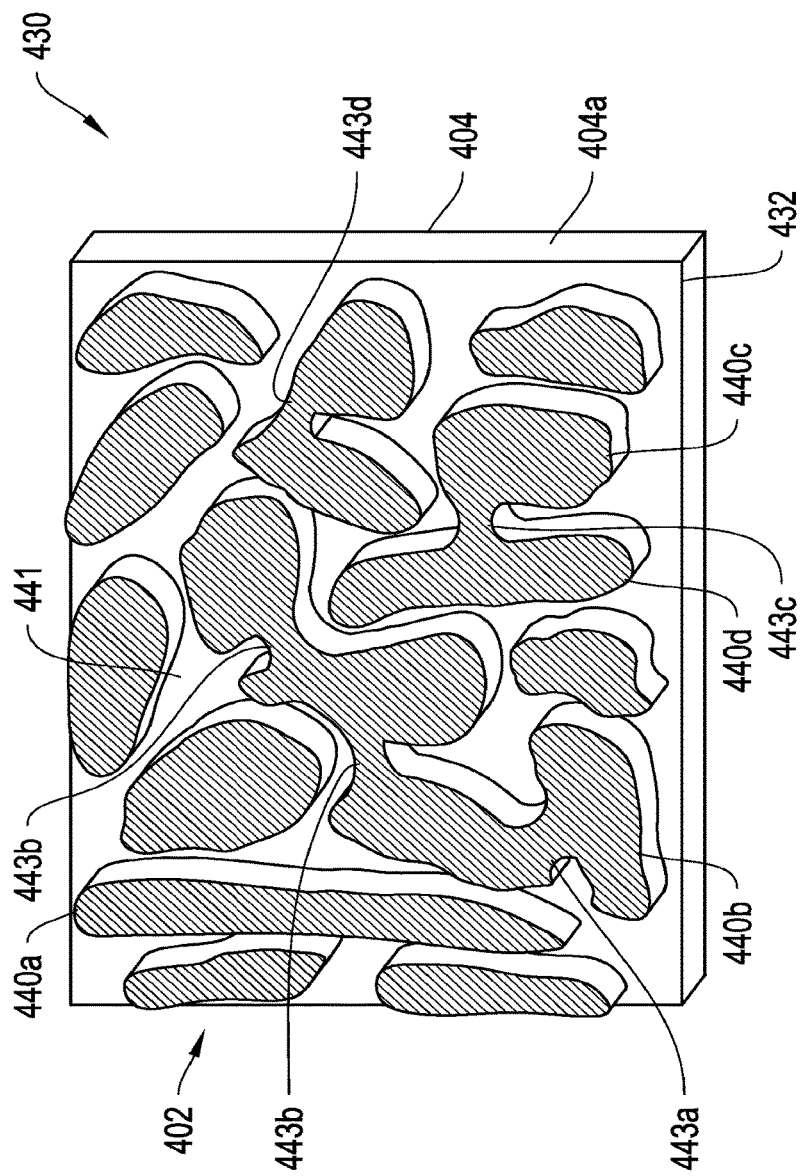
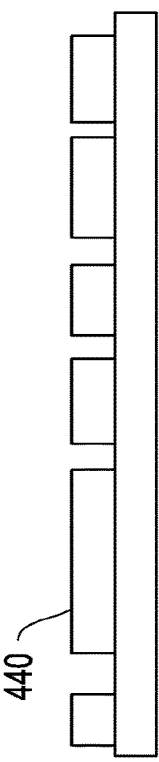
FIG. 16A
FIG. 16B

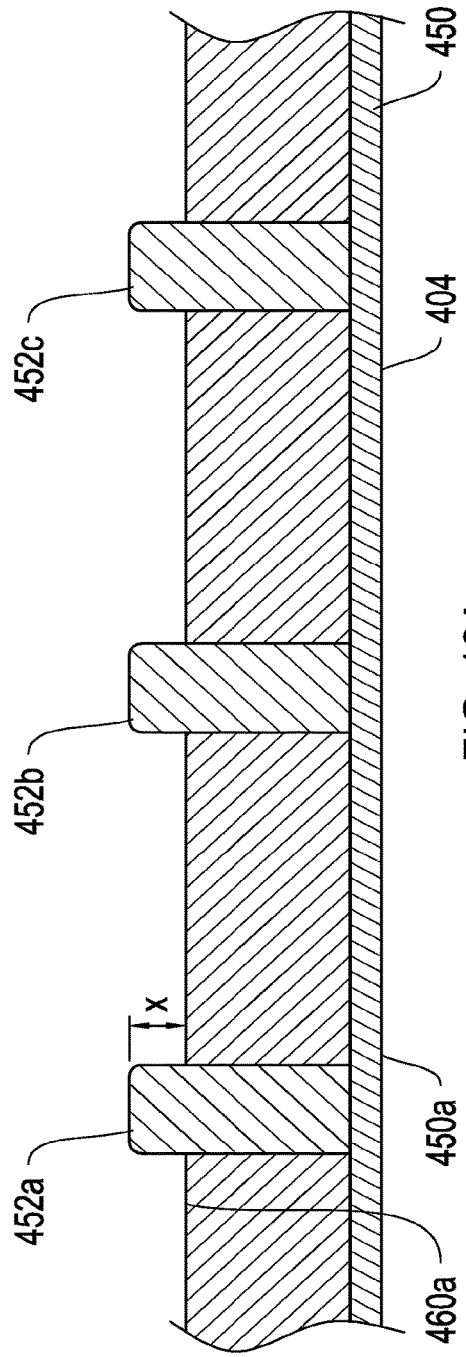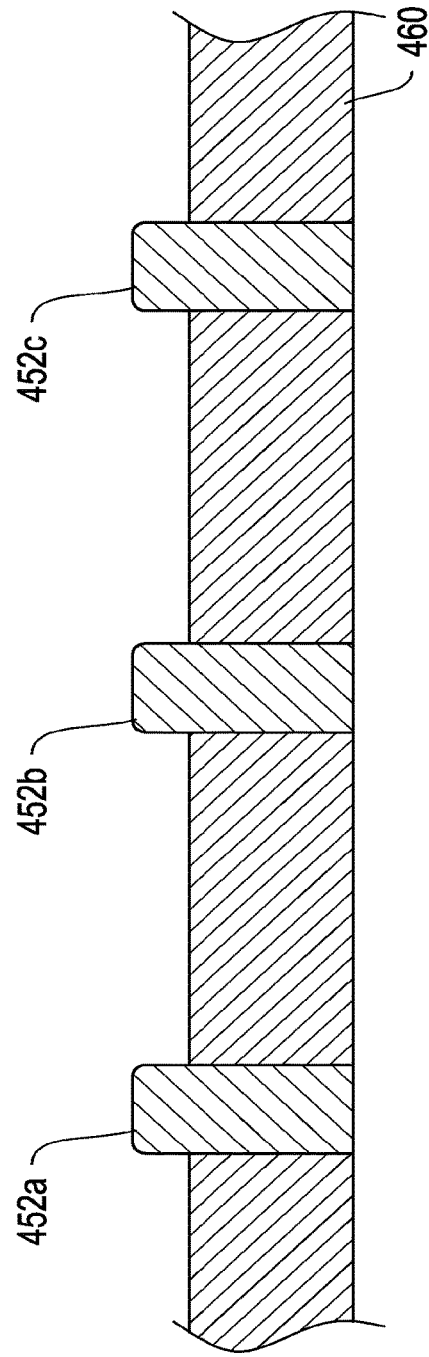

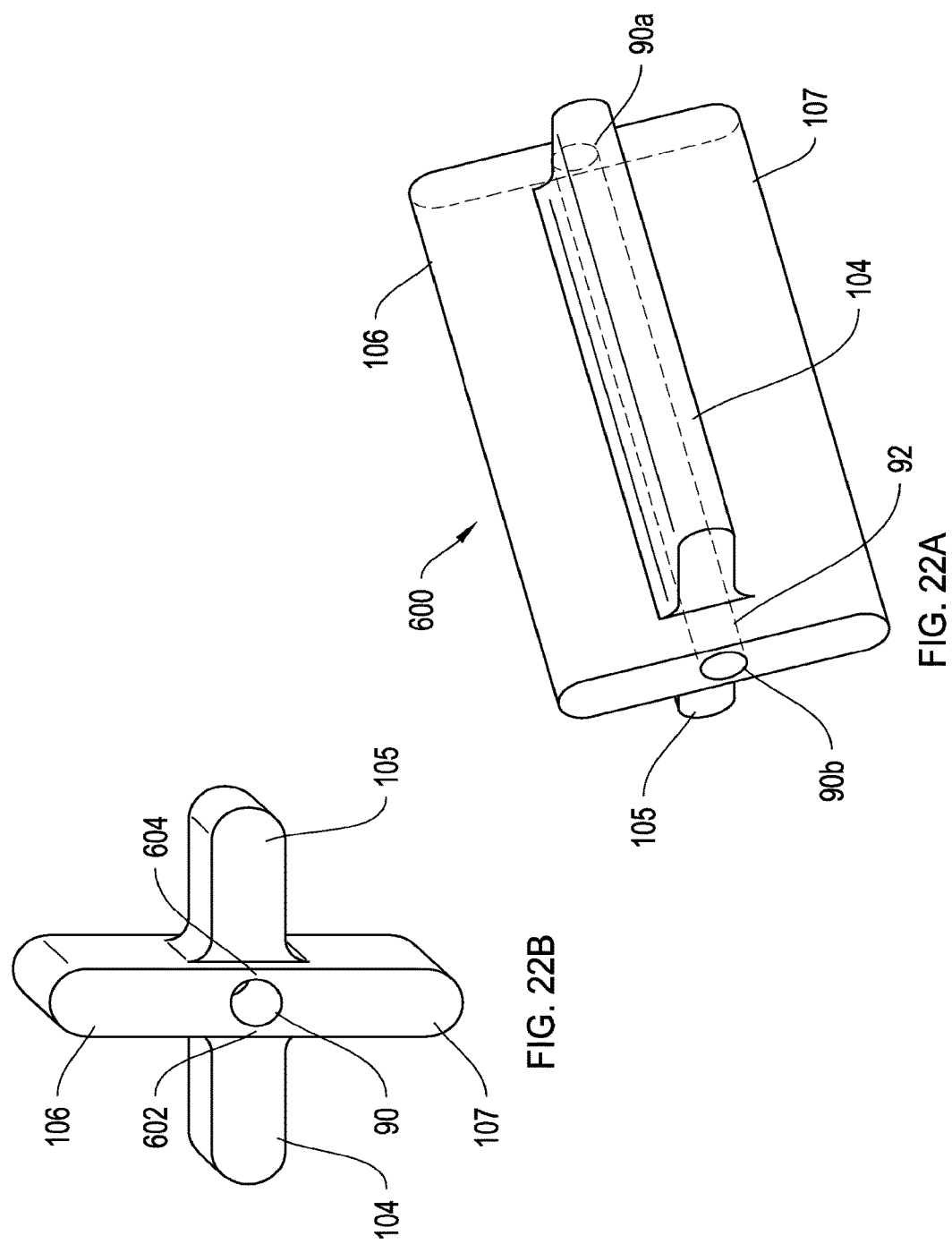

FRACTURE FIXATION SYSTEMS HAVING INTRAMEDULLARY SUPPORT

RELATED APPLICATIONS

This application is a division of United States application number 14/008,456, filed Oct. 22, 2013, now U.S. Pat. No. 9,060,823, which is a national stage filing under 35 U.S.C. §371 of International Application No. PCT/US12/30947, filed Mar. 28, 2012, which claims the benefit of U.S. provisional patent application No. 61/468,991, filed Mar. 29, 2011, the disclosure of each of which is hereby incorporated by reference herein in its entirety. International Application No. PCT/US12/30947 was published under PCT Article 21(2) in English.

BACKGROUND

Conventional devices and techniques used to treat bone fractures include external fixation structures, such as Illizarov and Taylor Spatial Frame, and internal fixation structures, such as plates, nails, pegs, screws, and other fixators. Each type of technique relies on providing proper stability to the bone so that it can heal naturally by normal growth and regeneration processes.

Fractures that involve load bearing bones, such as femurs and tibias, are particularly difficult to treat due to their substantial load bearing requirements. Devices used must provide sufficient axial, torsional and bending strength across the fracture site to support the loading. External fixation devices and methods typically encompass the fracture site and sit external to the patient's skin. They can be cumbersome, uncomfortable, carry a risk of infection, and limit ambulation and therefore often fail to fully satisfy a patient's desires for care and treatment.

Internal devices are installed on or in the fractured bone across the fracture site. An example is an intramedullary (IM) nail that is installed longitudinally into the intramedullary canal of a fractured bone. Some structures used in internal repair provide less than optimal biocompatibility and support for the patient's normal biological healing processes. Furthermore, after the fracture is healed, a second surgery may be required to remove the IM nail from the patient. This increases the risk of infection to the patient and cost to the healthcare system. Hence, considerable research and development has focused on techniques for replacing traditional fracture fixation devices with biodegradable (also referred to as resorbable, bioerodible, degradable, or bioabsorbable) implants. In the case of segmental defects or other serious fractures to a load bearing bone, such as a tibia or femur, managing the challenges recited above and others to find an appropriate balance of strength, biocompatibility, bioabsorbability and patient comfort can be particularly complicated.

SUMMARY

Disclosed herein are systems, methods and devices for repairing a fractured bone, for example a load-bearing bone (e.g., a tibia or femur) with a segmental defect or other serious fracture. Example devices and systems include load bearing support implants, such as sleeves and struts, for use in supporting a bone. A sleeve is placed inside the patient so it encases the fracture site and fixes and supports the fractured bone during healing. A strut is used to fill bone gaps, such as may arise from a serious segment defect. Struts are structured to be placed between bone segments to fixate the fracture and further support the restructured bone against axial, bending and torsional stresses that occur when the patient walks or otherwise loads the bone. One or more scaffold materials (e.g., putties or filler materials) may be disposed within the sleeve to secure the sleeve to the bone and stabilize the implant. One or more scaffold materials may be disposed within or about the strut to stabilize the strut within its fixation position between the segmented bones. The scaffold material acts as a scaffold for bone regeneration during healing. Sleeves and struts may be used separately or in combination.

In one aspect, a fracture repair implant is provided for use in repairing a load-bearing bone. The implant includes a biodegradable, load-bearing sleeve that supports ends of a fractured bone. The implant may include a biodegradable scaffold disposed within the sleeve. In certain implementations the biodegradable scaffold includes a plurality of interconnected channels, which may include at least one axial channel interconnected with at least one radial channel. In certain applications the scaffold is substantially brittle. The sleeve is arced, for example in the form of a tubular shell, and may be pre-formed in that configuration and then applied to the bone. The sleeve may be shaped so it tapers (e.g., between proximal and distal openings) or configured to otherwise provide a contoured fit to the bone fracture area. The sleeve may be a hard plastic or other stiff shell. In alternative configurations, the sleeve is formed from a pliable material, such as a polymer, that can be cured or otherwise formable into a hard shell. The hardening process may be applied after application of the pliable material to the bone, whereby the material is applied in a pliable state and cures so it hardens after application to the bone. In certain implementations the sleeve has at least one through-hole, such as an open window, along a longitudinal surface of the sleeve. Porous material such as foam may be disposed within the window. The porous material extends through the through-hole and provides a pathway between the bone or implant and muscle or soft connective tissue located external to the sleeve through which fluid can pass to the bone, and through which blood vasculature can grow.

In certain implementations, a biodegradable sleeve is provided with first and second openings (such as proximal and distal openings), wherein the first opening has a different cross-sectional shape than the second opening. In certain examples, at least one of a C-shape cross section and an O shape cross section are used for two respective openings of the sleeve. Each opening may be sized to receive an end of a fracture bone. The sleeve may also have at least one through-hole along a longitudinal surface of the sleeve. In certain embodiments the at least one through-hole is placed adjacent to a fracture in the bone. The sleeve is configured with cross-sectional dimensions needed to treat the bone. In certain embodiments the sleeve has regions with varying thickness, for example, a region with thicker walls that are placed at locations of high tension along the bone (e.g., posterior tibia) and thinner walls or regions of the sleeve placed at locations of the bone with higher compression (e.g., an anterior tibial region). The sleeve may have at least one of a pliable material and a pliable sheet.

In certain embodiments, a bone implant includes at least one longitudinal strut, constructed to be disposed between opposing faces of a segmented bone for providing at least axial support to the bone, wherein the longitudinal strut includes a central axis, and a wing with a surface that extends radially from the central axis. In certain implementations, the implant includes biodegradable material disposed on or about the longitudinal strut. The implant may have at least two wings with the biodegradable material disposed between the wings. The biodegradable material may be porous. In certain implementations, the longitudinal strut has a proximal portion configured to mate with a slot or hole formed within a face of a proximal segment of a patient's segmented bone, and a distal portion configured to mate with a slot or hole formed within a face of a distal segment of the patient's segmented bone.

In another aspect, a fracture repair system is provided having one or more of the implants disclosed herein. In certain implementations, the system includes a biodegradable sleeve configured with proximal and distal openings, with each opening sized to receive an end of a segmented bone, and at least one longitudinal strut. The strut is constructed to be disposed between opposing faces of the segmented bone for providing axial support and, in certain implementations, torsional strength to the bone. The strut has a proximal portion configured to mate with a face of a proximal segment of the segmented bone, and a distal portion configured to mate with a face of a distal segment of the segmented bone. The sleeve is positioned so it contains and envelops the strut and fracture site. For added stability, holes or slots can be formed within the opposing faces of the segmented bone, and end portions of the strut are configured to mate with such slots or holes. The strut can be configured according to any of those embodiments disclosed herein, or variations. For example, the longitudinal strut may include a central axis, and a wing with a surface that extends radially from the central axis. In certain applications, the sleeve has at least one through-hole, such as an open window, along a longitudinal surface of the sleeve. A porous matrix may be disposed within the through-hole. The porous matrix may also extend through the through-hole. In certain applications, the sleeve is unitary and molded without a longitudinal seam.

In another aspect, a fracture repair system is provided for use in repairing a load-bearing bone, comprising an implant configured to be disposed within a segmental bone defect, the implant having at least one longitudinal strut, constructed to be disposed between opposing faces of a segmented bone for providing axial support and, in certain implementations, torsional strength to the bone. The longitudinal strut may have a proximal portion configured to mate with a slot or hole formed within a face of a proximal segment of a patient's segmented bone, and a distal portion configured to mate with a slot or hole formed within a face of a distal segment of the patient's segmented bone. The longitudinal strut may include one or more proximal and distal wings with surfaces that extend radially about a central axis. One or more wings may be structured to fit within a mating hole bored into proximal and distal faces of the bone segments. One or more wings may include proximal and distal surfaces that abut the faces of proximal and distal segments, without penetrating into the faces. The proximal end of the longitudinal strut may have a different cross sectional shape than the distal end of the strut. The plurality of wings may be structured to form a well between them.

Certain fracture repair systems and devices include an implantable sleeve structure that surrounds the fracture site and is secured to the bone by a bioabsorbable putty or resin. The sleeve is sized to receive segment ends of a segmented bone and provide load-bearing support to the bone. In certain implementations, for example where a piece of the fractured bone is missing (e.g., from a serious segmentation wound), the sleeve encases and supports a resorbable intramedullary strut disposed between bone segments (e.g., to fill the gap from the missing bone) and resorbable porous putty filler materials (where included) as well as the bone itself. The sleeve may also be structured to further facilitate healing and support vascularization and further strengthen the bone during the healing process.

The sleeve is prepared in certain implementations as a unitary molded, cylindrical hollow tube of high-strength biodegradable material, such as a degradable polyester (e.g. PLA or PGA) or a high-strength polyurethane which has sufficient torsional, bending, and compressive strength to support the loaded limb against bending, axial and torsional forces that impact the limb as it is loaded. In certain implementations, the sleeve is cylindrical in shape, or may be tapered. The sleeve may be unitary, co-molded without a longitudinal seam. The sleeve may be a degradable polymer and may be sized to encompass a strut. In certain embodiments, the sleeve is used to contain and envelope a strut. Struts and sleeves disclosed herein may be used in combination.

In certain implementations, the sleeve includes a biodegradable foam dispersed in windows placed within the sleeve, where the foam protrudes through the walls of the sleeve and contacts the bone or an intramedullary implant, such as a strut. The foam is placed in the sleeve to act as a scaffold to aid vascularization of the defect area by allowing blood vessels to grow from the surrounding soft tissues and muscles into the fillers or putties on the strut. In certain implementations, all of the components of the systems and devices are biodegradable.

A biodegradable putty may be disposed on or about any of the struts disclosed herein. A biodegradable putty may be packed around at least one strut, preferably within a well or a plurality of wells. Any of the putties disclosed herein may be contained within any of the sleeves disclosed herein.

A wrap or sealant may be packed on or about any of the struts disclosed herein for insertion within an intramedullary area of a fracture. Any of the wraps disclosed herein may be contained within any of the sleeves disclosed herein. A wrap may include biodegradable foam. A biodegradable putty or resin may be disposed about any of the wrapped implants disclosed herein. Where a sleeve is used to secure an intramedullary implant with respect to a bone, putty or resin may be disposed between the implant (and bone) and the sleeve to further secure the implant and fill in space between the sleeve and the implant and bone. The filler resin or putty may have a different composition than the composition of resin and putty that packs about any of the struts.

Variations are also contemplated for biocompatible struts and sleeves, along with methods of application and manufacture. In certain embodiments, a shell can be prepared from a pliable material configurable into a sleeve about the wound site. The pliable material is moldable and therefore formable about the wound side, e.g., by hand molding. In certain examples, the material is provided as a wrap. The material is durable and may be curable into a strong, hard shell. Upon curing, the shell is sufficiently strong to bear the full load of the patient and, accordingly, fully supports the patient's bone load during the healing process. The material can be constructed and applied in various implementations. For example, the material can be formed from a wrap material that includes a first formable and degradable layer having an outer surface and an inner surface, and a second layer disposed on the inner surface of the first layer, the second layer being comprised of a formable polymer that is moldable into a sleeve that cures and forms a hard, biocompatible shell about the patient's bone. One or more through-holes, such as a window, can be disposed in the sleeve, for example in the first layer. One or more through-holes or windows may include a transparent portion of the first layer. One or more windows may provide an opening that extends through first layer, second layer, or both. Each window may be configured with biocompatible porous material such as foam, disposed over a surface of the window or even disposed within the window so it extends across the border of the shell after it has hardened.

The formable polymer can be applied to the first layer in either a single, unitary layer, or in a plurality of portions (or drops of material) that provide a plurality of portions spaced apart from each other on the first layer. The portions (or drops) may be formable and hardenable. Such structures may be combined with one or more windows, such that the portions of polymer are applied so as to surround or otherwise extend along one or more borders of the window. In some applications, a first portion (or drop of material) extends along a first border of a window and a second portions extends along a second border of the window. In a further implementation, a foam portion is disposed between two formable polymer portions, to provide a window structure to facilitate blood and fluid flow between the bone and external fluid. In certain implementations, the polymer layer has a first thickness, the foam has a second thickness, and the second thickness is greater than the first thickness.

One or more chemical catalysts or other curing agents (e.g., photo curing agents) may be disposed within the second layer to help facilitate hardening after the wrap is applied to the patient. In certain applications the catalyst is included in a concentration within the second layer sufficient to catalyze curing of the second layer in an exothermic reaction. In certain applications, the catalyst is selected from tin-based catalysts and zinc.

One or more layers may be used, and may be configured in a pliable flat sheet that is hand-moldable. The flat sheet is the rolled into a tube to surround the circumference of the patient's bone. The width of the one or more layers, together, may wrap completely about the circumference of the bone (such as the patient's femur), or may extend partially but not completely around a circumference of the bone when rolled into a tube. In certain embodiments, first and second layers are used and, together, have a thickness of between about 1 mm to about 10 mm. The thickness may alternatively be between about 4 mm to about 5 mm. In certain applications, the first layer of material is a biocompatible polymer, such as polycaprylactone, and the second layer is a biocompatible resin, which may comprise hydroxylapatite. A biocompatible filler may also be used with the polymer to improve the modulus of the polymer. For example, a filler such as hydroxylapatite or calcium phosphate could be suitable.

Certain methods of use include methods of repairing a segmented bone, comprising the step of securing an intramedullary implant, such as any one or more of those disclosed herein, between two bone segments. Method of setting a segmented bone fracture are also contemplated, including steps of inserting a longitudinal strut between opposing faces of a segmented bone, and applying at least one of a biodegradable sleeve and a pliable sheet about the longitudinal strut. Certain implementations of the methods include a step of injecting a biodegradable porous material in between the strut and at least one of the sleeve and the sheet. The porous material may be positioned between the bone and an inner surface of at least one of the sleeve and the sheet to allow fluid to flow from outside the sleeve into the bone. In certain implementations, the sheet covers a substantial portion of the circumference of the bone. Methods are also contemplated for repairing a bone fracture. In certain embodiments, the methods involve steps of positioning at least one of a biodegradable sleeve and a pliable biodegradable sheet (having a through-hole along a longitudinal surface of the at least one of the sleeve and the sheet around the bone), and injecting a biodegradable porous material in between the bone and at least one of the sleeve and the sheet. In the methods, the through-hole may be positioned adjacent to a fracture in the bone.

In certain embodiments, an implantable, load-bearing, orthopedic support sleeve is provided, having an interior tube, an exterior rounded configuration, and a midsection comprising a material of any of those described herein. The sleeve may be configured with a midsection that has a first thickness at a first location along the sleeve's length and a second thickness at a second location along the length. The varying thickness of the sleeve is selected to correspond with particular bone configurations (e.g., anterior and posterior tibial structures).

In certain implementations, a formable wrap, such as that described herein, is combined in a repair system with a longitudinal strut (such as those described herein) that is designed to fit between opposing faces of a segmented bone to fill a bone gap and provide at least one of axial support and torsional strength to the bone. The longitudinal strut is configured with a proximal portion that mates with a face of a proximal segment of a patient's segmented bone, and a distal portion configured to mate with a face of a distal segment of the patient's segmented bone. The strut mates directly with the faces of the segment. In certain implementations, the strut has one or more ends that are configured to fit within a slot or hole formed within a segment face (such as proximal, distal or both). One or more wings may be included on the strut. The one or more wings may include a surface that extends radially from a center axis of the strut. The longitudinal strut may also include a plurality of wings, with at least two wings form a well between them. In the system, the proximal end of the longitudinal strut may have a different cross sectional shape than a distal end of the strut. To form the system, the pliable flat sheet is preferably rolled into a sleeve, and the longitudinal strut is disposed within the rolled sleeve.

In another aspect, methods are included for setting a segmented bone fracture. Methods include applying a biocompatible material (such as those described herein) about the fractured bone to stabilize the fracture and support it during healing. In certain embodiments, the methods include installing a biodegradable sleeve, such as a hard shell, so that first and second ends of the fractured bone are disposed within the sleeve, whereby the sleeves envelops the fracture site. In certain implementations, the methods include steps of inserting a longitudinal strut between opposing faces of a segmented bone, and applying a biodegradable sleeve about the fracture and about the longitudinal strut. The step of applying a biodegradable sleeve may include applying a formable material, such as those described herein, about the fracture site (and the longitudinal strut, if used) so that the segmented bone fracture is enveloped by the sleeve. One or more windows may also be positioned within the material, and foam optionally applied as described herein. Methods include setting a bone fracture by steps of positioning opposing faces of first and second portions of a the bone to create an interface that facilitates bone growth between such faces, and applying a biodegradable material about the interface. Methods may include the steps of inserting first and second portions of a fractured bone within a bioabsorbable sleeve, and placing a bioabsorbable scaffold about the interface within the sleeve. The methods may also include the step of installing a longitudinal strut between first and second bone portions. Methods are included for repairing a segmented bone, comprising the step of securing an intramedullary implant to secure two bone segments. Methods are also included for configuring a surgical device. Examples include steps of inserting an implant, such as those disclosed herein, within a sleeve. The ends of the implant are aligned within the sleeve so as to be accessible through corresponding ends of the sleeve.

In certain applications, the material is circumferentially wrapped around the bone so that the material covers at least a portion of a circumference along a portion of the bone's length, and then at least one (preferably an inner, second) layer of the material changes its physical structure to harden and support the bone. A first layer (such as an outer layer) of the material can degrade after application to the bone.

The thickness of the wrappable material can be varied to correspond to particular bone structures being treated, as discussed herein. For example, tibial fractures could be treated by forming a formable wrap about the tibial fracture site but creating a first thickness in the anterior wrap, to correspond to the patient's shin, and a second thickness corresponding to a distal portion of the tibia, the second thickness being greater than the first thickness. In another aspect, kits are provided having materials that are configurable into implants and systems for use in repairing fractured bones. In certain embodiments the kits include a first material, such as a polymer that can be rolled out into a sheet having an outer surface and inner surface. The polymer is preferably formable into a first layer that is moldable and degradable. A second material is provided that can be configured into a curable layer that is formable and can be hand-molded about the bone. Upon curing, the second layer hardens into a hard shell and is biocompatible with the patient's bone. An intramedullary strut may also be provided, having a first and second end with a longitudinal axis. One or more wings may be provided to extend radially from the axis. The embodiments of struts and additional components discussed herein can be provided in the kits.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Further areas of applicability of the disclosed methods, systems and devices will become apparent from the detailed description provided hereinafter. It should be understood that the detailed description and specific examples, while indicating particular embodiments, are intended for purposes of illustration only and are not intended to limit the scope of the disclosure or any claims that may be pursued.

BRIEF DESCRIPTION OF THE DRAWINGS

The foregoing and other objects and advantages will be appreciated more fully from the following further description thereof. With reference to the accompanying drawings, these depicted embodiments are to be understood as illustrative and not as limiting in any way.

FIGS. 2C-2D depict a strut with a biocompatible scaffold having channels.

FIGS. 4A-4B depict perspective views of a sleeve in the form of a tubular shell that may be used as a support structure for an internal fracture fixation device.

FIGS. 5A-5B show the shell of FIG. 4A and FIG. 4B with biocompatible material protruding through windows in the shell.

FIGS. 6A-6B show components of a strut and sleeve system provided to repair and support a segmental defect within a bone.

FIGS. 7A-7F depict an example method of installing the system of FIGS. 6A and 6B.

FIGS. 11A-11C show an example of a sloped or tapered support shell that can be used in an internal fracture fixation structure.

FIGS. 12A-12B depict a biocompatible wrap material for forming a support sleeve about a bone fracture.

FIGS. 13A-13C depict an application of a wrap according to FIGS. 12A-12B to stabilize a bone fracture.

FIGS. 14A-14F provide a cross-sectional view of the process for applying a wrap to a bone as shown in FIGS. 13A-13C.

FIGS. 16A and 16B depict an implementation of a dual-layer wrap material for use in a fracture support implant.

FIGS. 19A-19B depict a cross-sectional view of the wrap with foam strips illustrated in FIGS. 18A-18B.

FIGS. 22A-22B depict side and top views of an embodiment of an intramedullary strut.

DETAILED DESCRIPTION

The figures illustrate examples of internal fixation devices used to stabilize a fractured limb. In preferred implementations, the devices have biodegradable implants that provide support and at least one of torsional, axial and bending strength for treating a fractured, load-bearing bone. In certain implementations, the devices include a sleeve disposed about the fracture site. In certain implementations, the devices include a strut and sleeve in combination. Procedures for surgically installing the devices are also contemplated.

Figure 1:
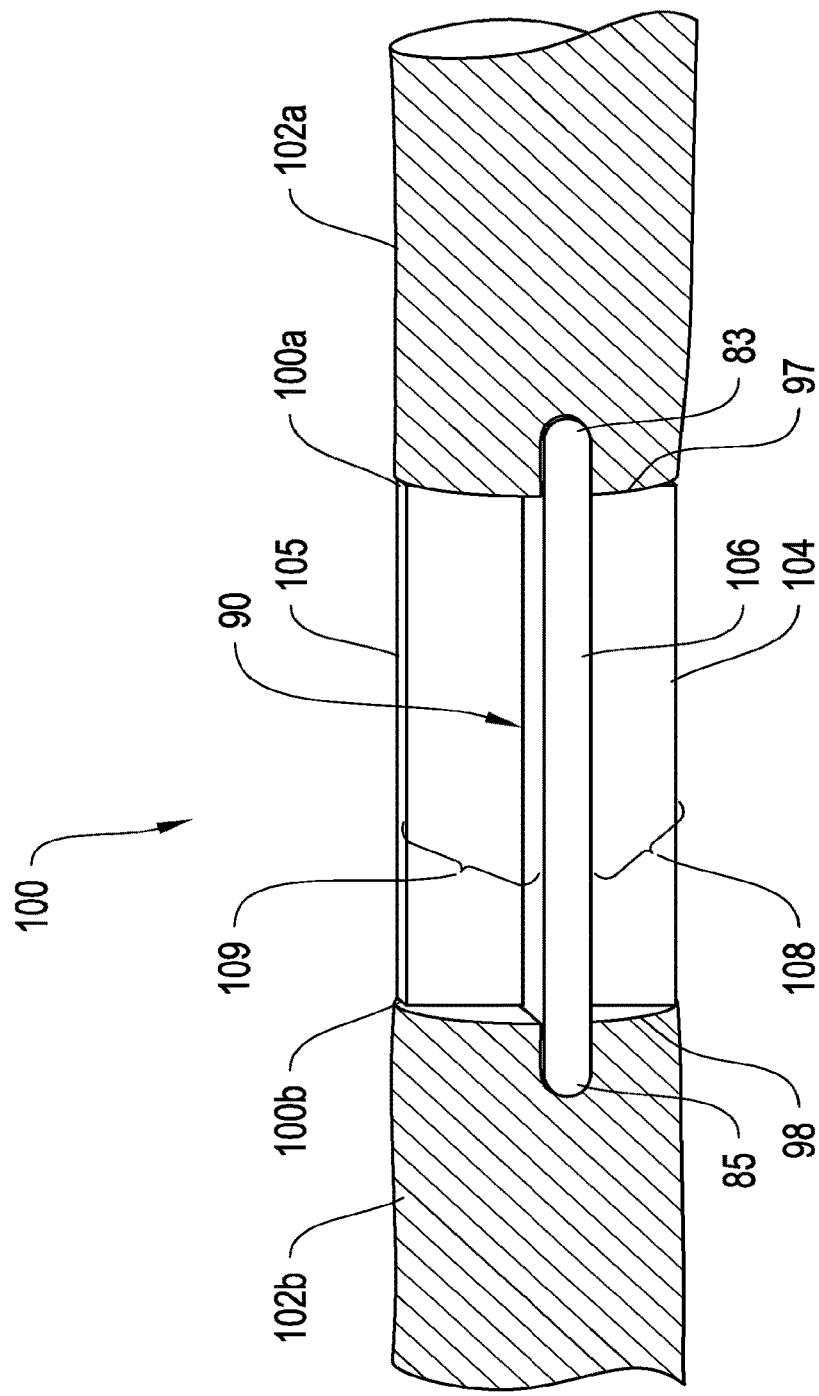
FIG. 1 shows a side view of a segmented bone with an intramedullary strut disposed between segment faces of the bone.
Figure 2B:
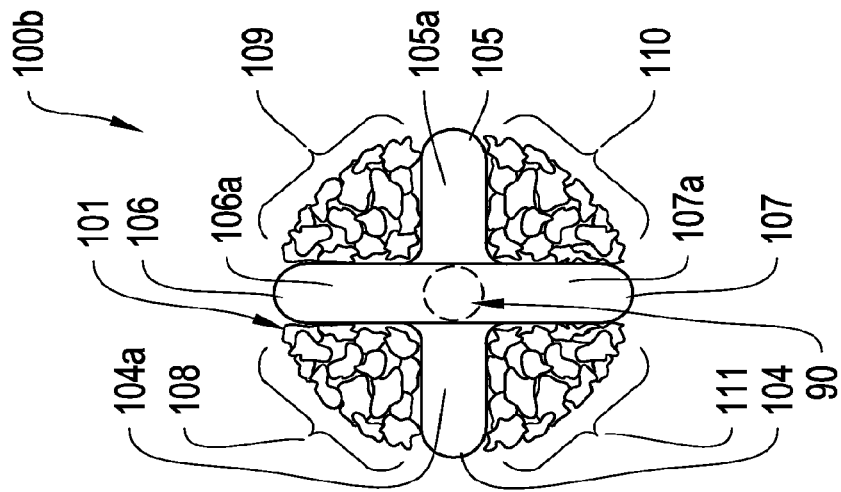
FIGS. 2A-2B show a side and top view of a strut with biocompatible particles.

FIG. 1 shows a fractured bone 102 having proximal 102a and distal 102b segments, resulting from a serious fracture such as a desegmentation fracture from a battle wound. A degradable intramedullary implant is disposed between the segments. The implant shown in FIG. 1 is a strut 100 having proximal 100a and distal 100b ends which are fitted to the segmented bone faces. As also seen in FIG. 2B, the strut 100 has a central hub 90 or axis and a plurality of longitudinally extending wings 104, 105, 106, and 107 co-molded with the hub 90 or otherwise joined to it. Disposed longitudinally along the central hub 90 and between each adjacent pair of wings is a well, shown as wells 108, 109, 110, and 111.

Figure 2A:
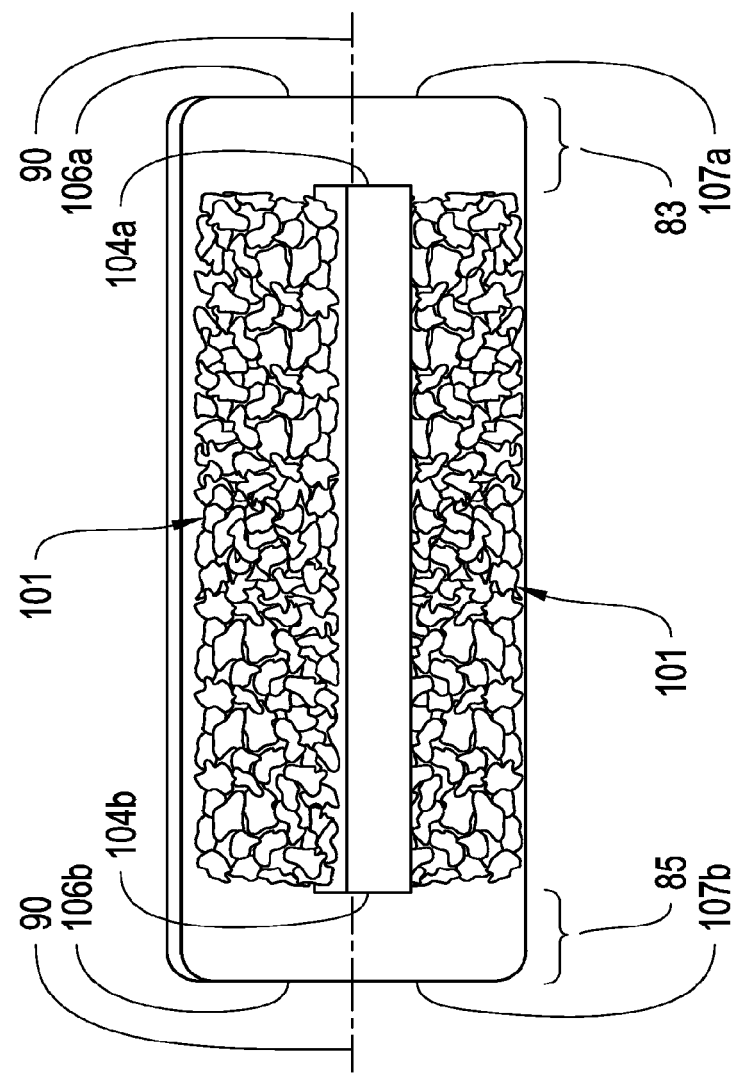

The central hub and wings, which extend away from the hub in different directions, provide a strut that supports a load on the bone substantially across the segment face, thereby improving the implant's stability and strength. As shown, the opposing wings 106 and 107 of the strut 100 are longer (the "long wings") than the opposing wings 104 and 105 (the "short wings"). The proximal ends of the long wings 106 and 107 form a continuous proximal tip 83 and the distal ends form a continuous distal tip 85, with tips extending beyond the respective proximal and distal ends of the short wings 104 and 105. This is shown in FIG. 2A, where the proximal tip 83, formed of the proximal end 106a of wing 106 and the proximal end 107a of the wing 107, extends proximally further than the proximal tip 104a of the wing 104 (or 105, not shown). Similarly, distal tip 85, formed of the distal end 106b of wing 106 and the distal end 107b of wing 107, extends distally further than the distal tip of the wing 104b (or 105b).

In operation, the strut 100 mates with the bone segments in a way that enhances the implant's axial and torsional strength. As shown in FIGS. 1 and 2A, corresponding faces 97 and 98 of the bone segments are bored or cut with slots that fit tightly with the proximal and distal tips of the long wings 83 and 85, respectively. This fitted structure, on both sides of the strut 100, allows the implant to carry the axial load and a torsional or twisting load between the distal and proximal ends of the strut. The ends 104a, 105a and 104b, 105b of the short wings abut the faces 97 and 98 of the segments 100a and 100b, respectively, to help axially stabilize the strut but do not penetrate the faces of the bone segments.

The structure of the strut can vary, for example in the number and arrangement of the wings as well as the structure of the connection between the strut and the bone segments. The strut 100 has four wings that form a cross-section in the form of a "+" but with two wings that are longer than the other two. The slots 93 and 94 are each cut in the shape of a single channel that extends substantially across the faces 97 and 98 of the segment and receive the tips 83 and 85 of the two longer wing pairs. In alternative implementations, additional wings could be extended about the hub 90 to form a more complex strut end. For example, a third wing could be extended, being molded to the same length as the tip 83 (or tip 85), and the slot on the bone face 97 could include a branch channel, forming a "Y" shaped slot, that accommodates the extended third wing. In other alternatives, all four wings 104, 105, 106 and 107 (or at least three of them) could be extended and molded to the same length about hub 90, forming a molded head with four wings. A corresponding slot with a "+" shape (see FIG. 10) or other suitable shape would then be cut into the face of the bone segment to receive that head, seating the central hub and a tip of each extended wing in a secure arrangement. In still other implementations, a proximal portion of the hub 90 near the proximal end 100a of the strut 100 (or a distal portion, near the distal end 100b of the strut 100) could be removed, and the long wings could be separated and extended from the remaining hub portion like the fingers of a claw, having a plurality of radial-spaced tips that extend beyond the hub 90 and interface with the corresponding faces 97 and 98 of the segmented bone. To accommodate the extending tips, corresponding slots could be cut within the faces 97 and 98 as individual holes, and each hole would align and mate with a corresponding tip.

The strut 100 is preferably made of a degradable material, such as high-strength polyurethane, which allows it to degrade over time while bone regrowth and regeneration occurs across the fracture site. This bone regrowth and regeneration may be facilitated by biodegradable materials, such as a porous scaffold, that are applied in conjunction with the strut 100. Examples of a porous scaffold may include putty particles or resin. FIGS. 2A and 2B show the strut 100 having a biocompatible, biodegradable porous putty 101, as an example of a scaffold, packed within the well areas 108, 109, 110 and 111 between the wings of the strut 100. An example of putty 101 includes hydroxylapatite (HA) particles mixed with a polyurethane resin, creating a porous mixture with one or more particle lumps mixed with the resin, forming a scaffold to align with the wells of the strut 100. Example putty materials are disclosed in published patent application PCT/US2009/051715. Particle size ranges that may be suitable for the putty materials, particularly in examples using the HA particles can range from about 5 µm to about 4,000 µm, however more particularly preferred particles of HA have a diameter that is greater than 10 µm or in some implementations from about 800 µm to about 2,800 µm. Other example particles may be used, such as calcium phosphates, orthophosphates, mono-calciumphosphates, di-calciumphosphates and other phosphate materials, other than HA (or in combination). In certain preferred implementations, the particles stick together by the resin but not all of the space between them is filled, thus providing a scaffold with open voids between the particles that allows blood to flow and bone to regrow and regenerate between the faces 97 and 98. This provides a path for the bone to grow between the segments as healing occurs.

Alternative biocompatible scaffolding material may be used. For example, FIGS. 2C-2D depicts a scaffold 103 disposed about an intramedullary strut similar to strut 100. The scaffold 103 contains a plurality radial pores 114 and axial pores 113, wherein one or more radial pores interconnects with one or more of the axial pores, to form a series of interconnecting channels within the scaffold 103. Also shown, four axial channels 112a-112d extend along the interface between the scaffold 103 and wings of the strut 100. These larger channels 112a-112d allow the delivery of biologics, or other drugs to the fracture repair site. The scaffolding material 103 is in certain implementations a brittle but stiff material, which allows blood and other fluids to flow between the fracture site and the patient's circulatory or lymphatic fluid systems.

In certain applications, the scaffolding 103 is made by a 3-D plotter from a CAD model. In practice, the CAD model is used to design the size and the structure of the scaffold to fit with the patient's fracture site. The scaffold 103 may also contain variable thickness areas, such as roll 103a, for added stability and strength. In certain applications, the scaffold 103 is contoured or textured to fit within a gap of a segment of the fracture to replace missing bone. The scaffold 103 may be cylindrical or may be designed to match the contouring and the shape of a bone where it is applied. In certain applications, the scaffold 103 is prepared by the technician or surgeon identifying by tactile feeling or by visually determining the needed structure and contouring, and then programming corresponding design dimensions and coordinates within a software system to generate a CAD model based on that needed structure and contouring. One or more pores and channels are also preferably programmed within the CAD model and included in the design. The 3-D plotter or rapid prototyping machine is used to generate the scaffold 103 from the CAD model. In certain applications, the scaffold 103 is used in lieu of the biocompatible putty shown in FIGS. 2A-2B.

Example scaffolding 103 is made of HA or tricalcium phosphate (TCP), or a combination thereof. In certain implementations, the scaffold 103 is designed to have a predetermined level of porosity and connectivity between its pores or channels. For example, it may have a 20 to 50 percent porosity. In some implementations the porosity is more finely determined, for example about 30 to about 40 percent, or about 35 to 36 percent porosity. Connectivity between the channels will be at a desired level, for example 90 to 95 percent, or even 95 to 99 percent, for example 98 percent connectivity. The pore sizes may also be adjusted as desired, for example certain applications would use pore sizes of 400 to 600 micrometers.

Figure 3B:
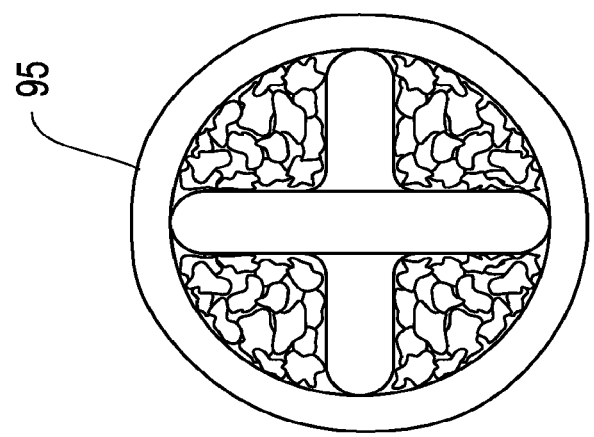
FIGS. 3A-3B show side and top view of a strut and putty support structure wrapped within a biocompatible foam prior to implantation within a patient.
Figure 3A:
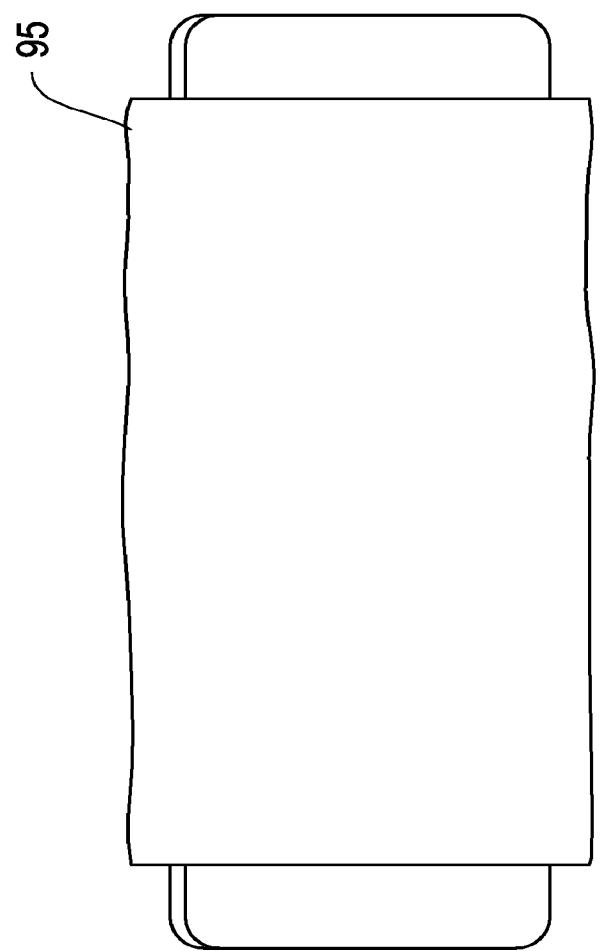

FIGS. 3A and 3B illustrate a biocompatible, biodegradable wrap 95 applied around the strut and putty combination of FIGS. 2A and 2B. The wrap 95 may be a flexible polymer foam, such as flexible polyurethane foam or other biocompatible material. Wrapping the strut in materials such as biodegradable foam can facilitate blood flow around the fracture, for example blood flow passing between the segments of a fracture, thereby encouraging enhanced bone regrowth across the fracture site.

In certain implementations, a biocompatible sleeve is used to secure a fracture site. The sleeve may be used by itself or in conjunction with an intramedullary strut. For example, a sleeve may be used to further secure the strut 100 within the intramedullary canal of the bone, between the bone segments 102a and 102b. FIGS. 4A-5B illustrate an example sleeve in the form of a stiff biodegradable shell. As shown in FIG. 4A, the sleeve 120 is formed as a cylindrical tube of high-strength polymer or composite having a thickness 124 and at least one window 122 (a plurality are shown) which is positioned in use to surround the strut 100 when it is installed between the bone segments. The window 122 is a through-hole in the sleeve 120, but may include a clear coating across the sleeve 120. In alternative implementations, the sleeve 120 may be formed with an elliptical or D-shaped cross section to conform more closely to oblong or D-shaped bones. The elliptical or D-shaped sleeve may also be tapered. The windows (in the through-hole embodiments) provide an opening through which blood and new blood vasculature can flow into the sleeve and thereby into contact with the bone, to help nourish it during healing. Variations on the number and location/shape of the windows can be provided, as desired.

Suitable sleeve materials may include, for example, a biodegradable, high-strength polyurethane. Other examples of suitable sleeve materials include biodegradable polyesters (e.g., polylactide, polyglycolide), blended materials containing two or more different biodegradable polymers (e.g., PLA, PGA together), and biodegradable composites, such as polyurethane combined with HA. When using blended or composite materials, components may be selected so the sleeve has a desired stiffness without becoming too brittle. For example, composites that include a polyurethane and HA typically increase in stiffness as the composition of HA increases, but they also become more brittle and therefore potentially have a shorter useful life. In certain implementations, the composition of HA is selected, for example, to be within the range of about 20% to about 50%. In one implementation, the sleeve is structured from a composite having about 70% polyurethane and about 30% HA.

As shown in FIGS. 5A and 5B, a biodegradable foam 130 is disposed within the windows 122 and serves many functions including facilitating vascular remodeling from one site to another. The foam protrudes into the internal cavity 131 of the sleeve 120 through the window 122 until it abuts the bone segment or the strut 100 (or both). As shown in FIG. 5B, the foam 130 has portions 130a that extend outside to external side 133 of the sleeve. The foam is biodegradable and provides a scaffold for vascularization and bone regrowth and regeneration between the bone segments. The windows may also be structured to permit new blood vessels to grow into the sleeve, through the foam and into contact with the strut or bone. Such new vessels may originate from the muscle and soft tissue that surrounds the sleeve, and from there grow radially into the foam to contact the strut or bone, or the vessels may originate from the ends of bone segments 102a and 102b and grow longitudinally along the bone and strut, within the sleeve. The foam also impedes leakage of putty or resin from the internal space of the sleeve. In certain implementations, the sleeve 120 includes through-holes for injection of resin or other materials into the sleeve to enhance the contact, for example, between the sleeve 120 and the bone segments. An example of suitable foam may include open cell foam. Any other porous materials may be used if it has connected porosity suitable for blood vessel growth.

The sleeve 120 is molded as a unitary cylindrical structure. It may be manufactured, for example, by injection molding or other methods known to one skilled in the art. The unitary structure strengthens the sleeve by minimizing the weak areas along its length. Alternative implementations may provide the sleeve in a clam shell-type structure that has a top and a bottom portion clamped together or buckled together by biodegradable latches, ties or screws. The sleeve 120 and the foam 130 may also be manufactured or molded as an integral device. The sleeve 120 may also have selective portions which are porous and raised above the sleeve surfaces 131 and 133.

FIG. 6A illustrates the components of a surgical system that may be used to repair the bone segments 102a and 102b of a fractured bone 102 and begin the healing process for the patient. The components of the surgical system illustrated in this figure include an intramedullary implant 140 having an internal strut 100 packed with biodegradable putty 101 and biodegradable foam in wrap 95, similar to the examples described above. Also included is a sleeve 120 that extends about the strut and bone interfaces, having a plurality of windows 122 and biodegradable foam materials protruding through the windows, similar to the sleeve described above. Proximal and distal wraps 150a and 150b or other materials such as bone wax or sealants may also be included for containing the contents within the sleeve 120.

Figure 6B:
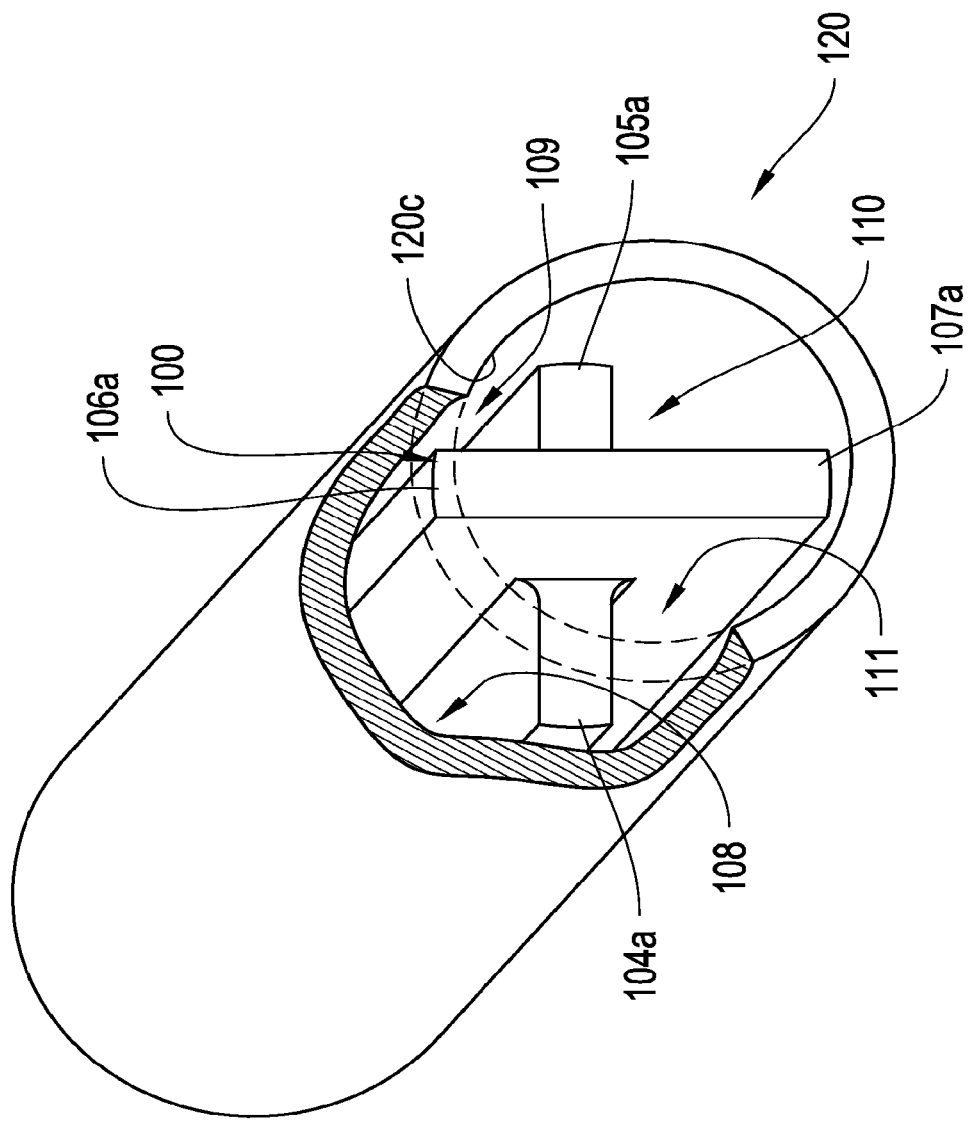

FIG. 6B illustrates an alternative implementation of the strut 100 and sleeve 120 as may be used in the surgical system shown in FIG. 6A. In particular, the strut 100 is co-molded with the sleeve 120, such that the entire combination forms a contiguous, co-molded bioerodible polymer structure. As shown, each of wings 104, 105, 106, and 107 are co-molded together and with the inner surface 120c of the sleeve 120. Also shown, well areas 108, 109, 110, and 111 remain disposed between the wings 104, 106, 105, and 107, respectively. However, no outer wrap 95 is included. The well areas 108, 109, 110, and 111 can receive biocompatible, biodegradable putty or particles, such as the putty 101 described above. The unitary structure with strut 100 and sleeve 120, co-molded together, is structured to fit between the bone segments 102a and 102b. For example, extended wings 106a and 107a of the strut 100 can be disposed with the slots 93 or 94, of bone segments 102a and 102b, as described below. The strut 100 is optional, and the sleeve 120 can be applied with putty 101 to provide load bearing support.

Figure 7A:
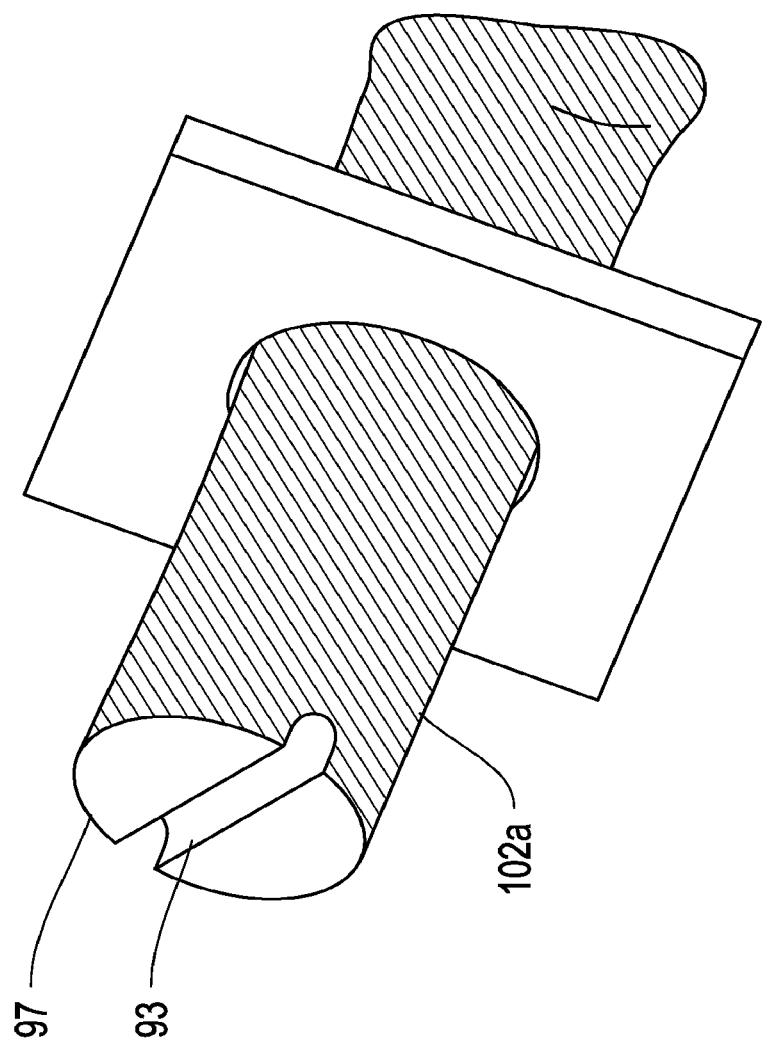
Figure 7B:
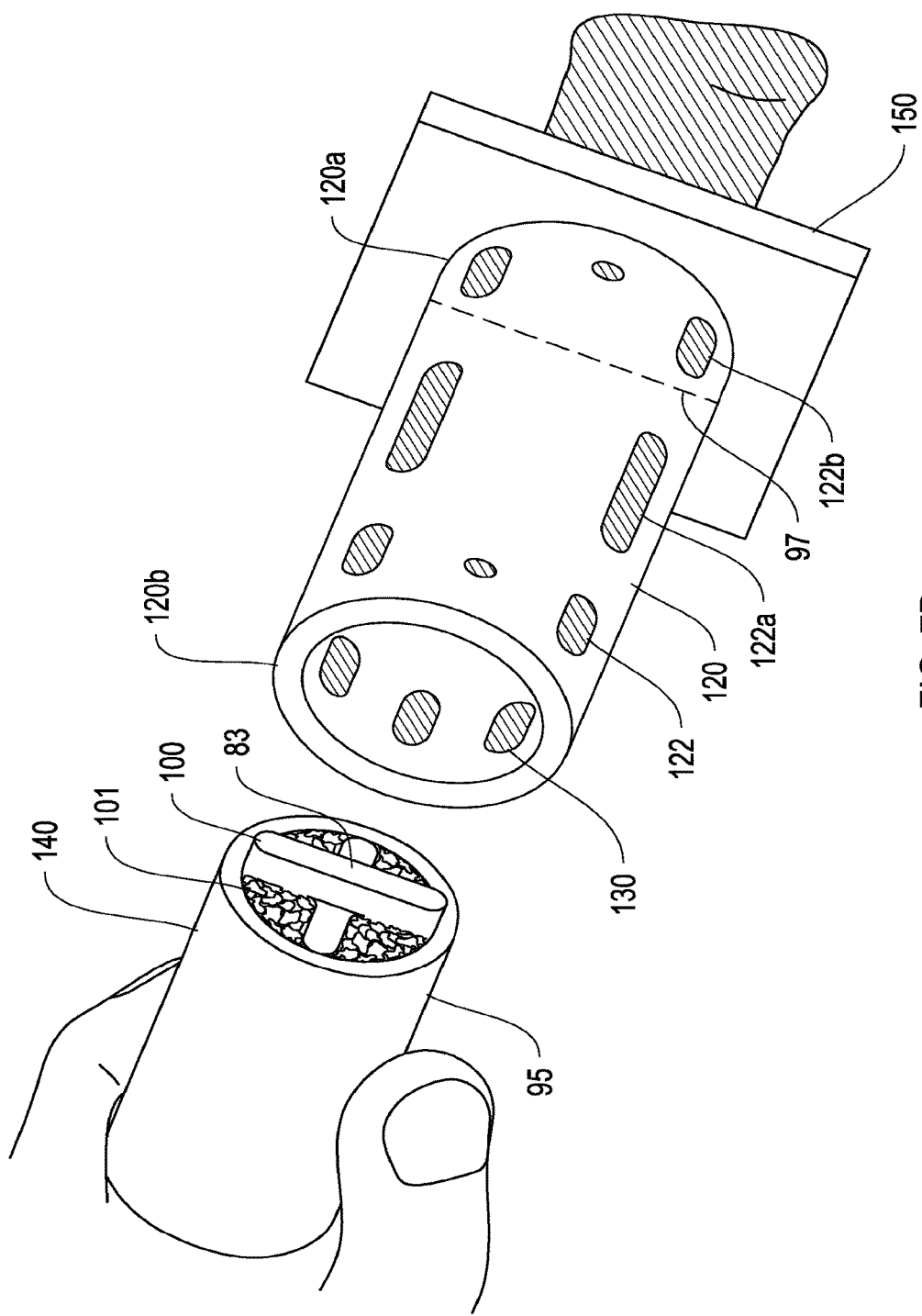

FIGS. 7A-7F depict an example surgical procedure used to prepare a segmented fracture site and install an implant to repair the site. In a first step, the bone segments 102a and 102b are prepared. As shown in FIG. 7A, a slot 93 is bored within the proximal face 97 of the bone segment 102a, generally bisecting the intramedullary canal. A corresponding slot 94 is bored within the center of the face 98 of the other bone segment 102b. The slots 93 and 94 are sized to snugly receive corresponding strut ends (for example tips 83 and 85) of the strut 100. Examples of other preparations may include roughening the bone so that the resin, when set, has a mechanical engagement with the bone, and creating holes or divots in the bone that can receive resin, thereby providing a mechanical engagement as resin fills the holes or voids. In implementations that do not use a strut, the bone faces may also be sized, trimmed, resurfaced or otherwise modified so as to fit together as seamless as reasonably practicable, creating a direct interface between the facing surfaces that facilitates bones re-growth and repair.

After the segments are prepared, which may also include drying or removing of periosteum or other preparations, the surgical system is installed. To install the system, where a strut is needed to fill a gap, the strut 100 is provided with packed porous putty as described above (FIGS. 2A and 2B) or other porous scaffolding and optionally wrapped in a biodegradable wrap 95. The sleeve 120 is prepared with windows and foam 130 installed so as to protrude into the windows. The foam 130 preferably also protrudes internally within the sleeve 120 so it contacts the bone surface or the strut (or the wrap 95), thereby creating a path for blood or new blood vasculature to grow and extend from the exterior of the sleeve, through the windows, and into contact with the bone and implant. In that configuration, resin disposed within the sleeve (as discussed below) can flow within the sleeve and around the internally protruding foam, but will not occlude the path between the window and bone or strut.

The sleeve (and strut) are then installed in the fracture site. To perform the installation, in one implementation, the proximal end 120a of the sleeve is slid over the face 97 of the proximal segment 102a (FIG. 6, 7B). The implant 140 is then installed through the distal end 120b of the sleeve 120 so that tip 83 aligns with and fits within slot 93, prepared within the face 97 of the bone segment. The implant 140 may need to be twisted and maneuvered within the sleeve until the tip 83 of the strut is in place within slot 93.

Figure 7D:
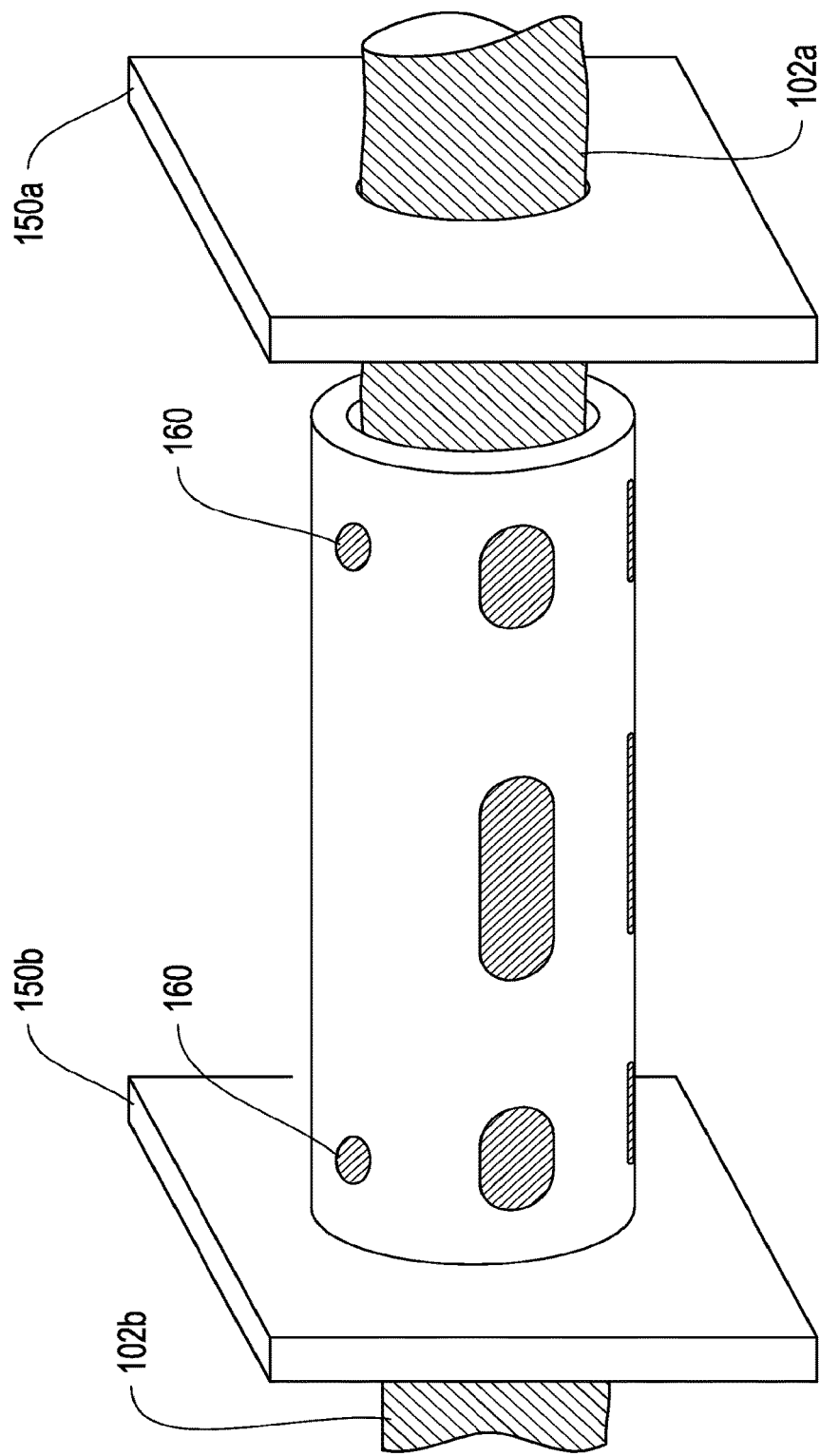

After the implant 140 is installed within the sleeve, the distal bone segment 102b is then inserted within the sleeve and positioned until its respective slot 94 aligns with the distal tip 85 of the long struts on the distal end of the implant 140. The surgeon pushes the segment 102b into the sleeve so that the slot 94 presses onto the tip 85 and fits snugly. FIG. 7D shows the implant fully encased within the sleeve. The sleeve may be translucent to allow visibility into the location and placement of the implant. The implant may be fitted within the sleeve so that the interface 97 extends between windows (122a and 122b) under solid sleeve internal surface, not exposing the sensitive interface through the windows, to help protect the interface between the bone surface 97 and the implant. The wraps or sealants may also be applied during a surgical procedure after positioning the sleeve on the bone. One of skill in the art will appreciate that the order in which the installation steps are performed can vary. In implementations that do not require a strut, the segment ends 102a at 102b are each placed within respective ends of the sleeve 120 and joined, while within the sleeve 120, so that their respective opposing bone faces join directly together to form a bone-bone interface enveloped within the sleeve. Techniques for resurfacing and modifying the faces may be applied, for example as discussed above.

Figure 7E:
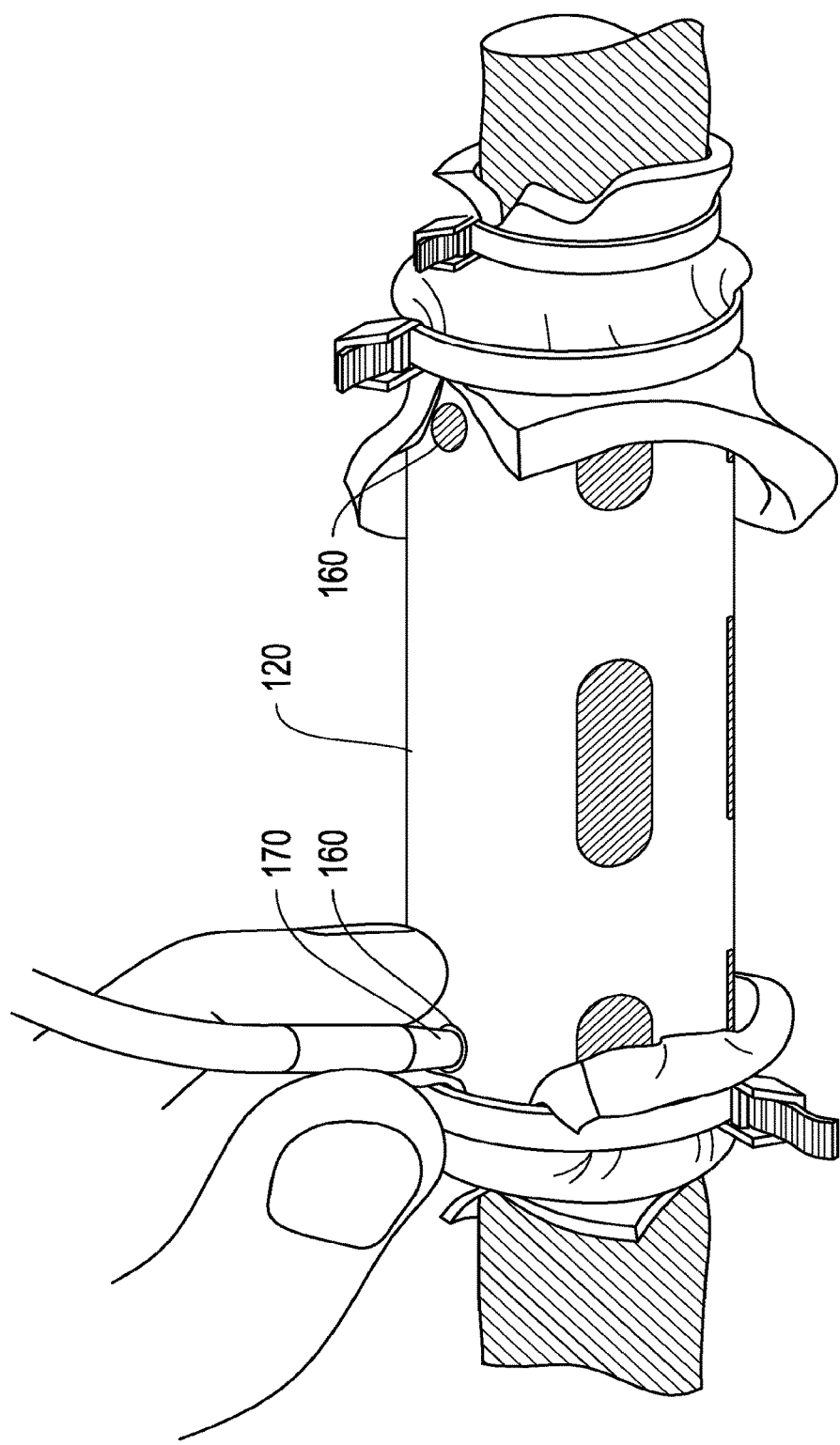
Figure 7F:
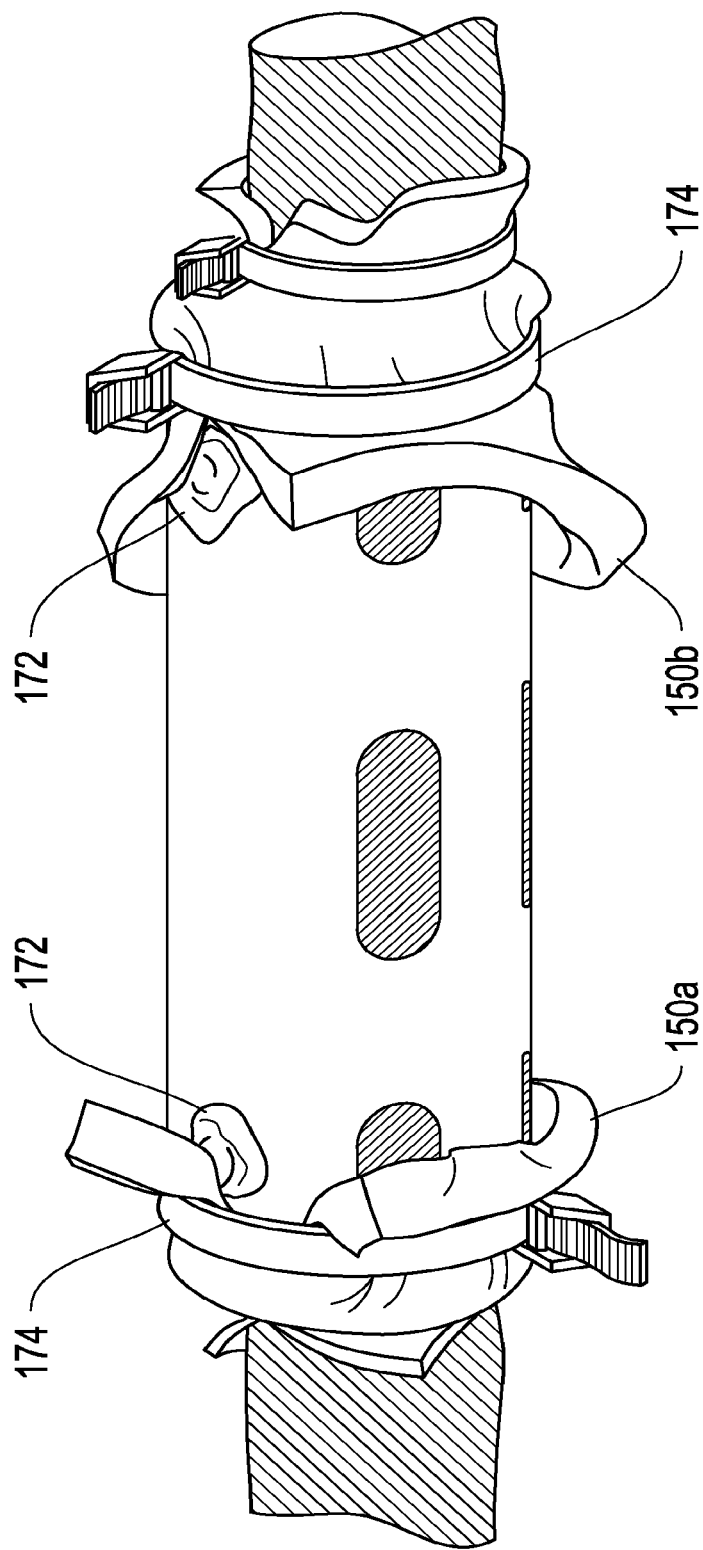

After securing the bone segments (and the implant, when used) within the sleeve, space will likely remain between the implant 140 (or bone) and the interior surface of the sleeve. That space may be filled with resin or putty to further support and secure the bone within the sleeve. To ensure the resin does not leak out from the ends of the sleeve, the wraps 150a and 150b or other bone sealants may be used to close off the ends of the sleeve. The wraps 150a and 150b are pulled down over the corresponding ends of the sleeve 120 and secured radially about the ends of the sleeve by twist tic, Tic Vac, polymer, Cerclage wire, suture, elastic material, or other securing mechanism 174 that compresses radially. A connecting member, such as a Luerlock may also be used to engage the dispenser and the sleeve as illustrated in FIG. 7E. The sleeve 120 has one or more holes 160 which receive a dispenser that contains additional putty or resin. The dispenser 170 dispenses the putty or resin through the holes 160 and inside the sleeve, so it flows around the implant 140 and the bone ends which are overlapped or covered by the ends 120a and 120b of the sleeve. Polyurethane resin may be suitable resin. Examples of other putty and resin that may be used are disclosed in published patent application PCT/US2009/051715. After the putty or resin is injected inside the shell, the holes 160 may be sealed with a bio-degradable sealant or glue 172 or plug, or it may also sealed with the resin or putty. The wraps and tie mechanisms may be removed once the resin is set. An example is shown in FIG. 7F.

In certain implementations, all of the components, including all materials used inside the implant are biodegradable, so that over time the entire surgical system erodes away and leaves a healed bone as bone regrowth and vascularization occurs. In other implementations, the system may be used in combination with one or more non-degradable materials, such as an intramedullary nail, plate or screw, or an external fixator (for example a pin or rod as described in FIG. 23 of patent application PCTUS2009/051715).

Figure 8:
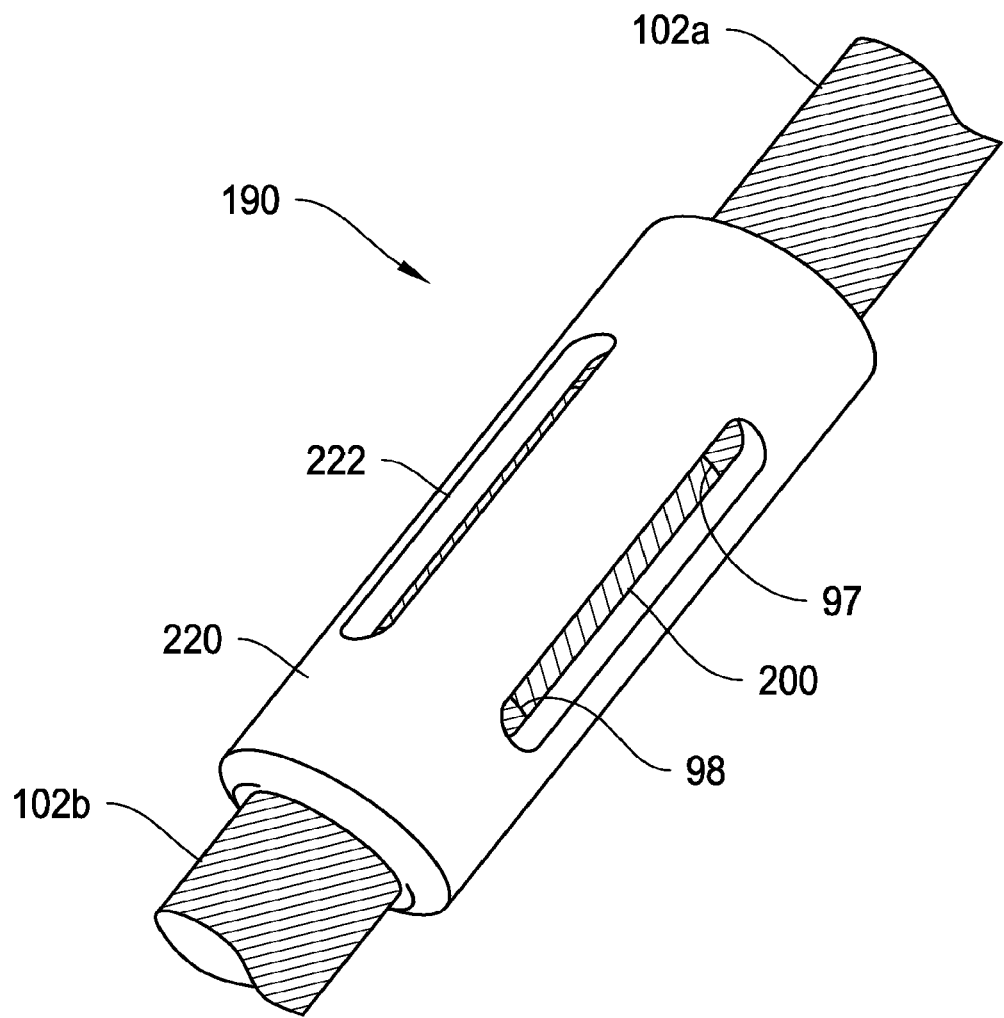
FIG. 8 depicts an example intramedullary strut and shell used to address a segmental defect in a bone.

FIG. 8 illustrates an implant structure 190 having a strut and sleeve combination similar to the structures described above. As shown, a strut system 200 is disposed between two bone segments 102a and 102b and encased within a sleeve 220. The strut system 200 is similar to implant 140, in that it includes one or more rigid, elongated wings and a biodegradable packing material that wraps around the wings and facilitates revascularization and bone regrowth between the segments. As shown, the sleeve 220 is a cylinder similar to sleeve 120 described above, but includes longer windows 222. The longer windows provide a longer path for blood to flow into the sleeve and into contact with the bone. The windows 222 also expose the interfaces between the strut system 200 and the faces 97 and 98 of the bone segments 102a and 102b, in contrast to sleeve 220, which has smaller windows 122 that are dispersed along the cylindrical wall but do not expose the interfaces between implant and bone segment faces 97 and 98. A sleeve with longer windows, such as window 222, may also be desirable to assist in alignment and placement.

Figure 9:
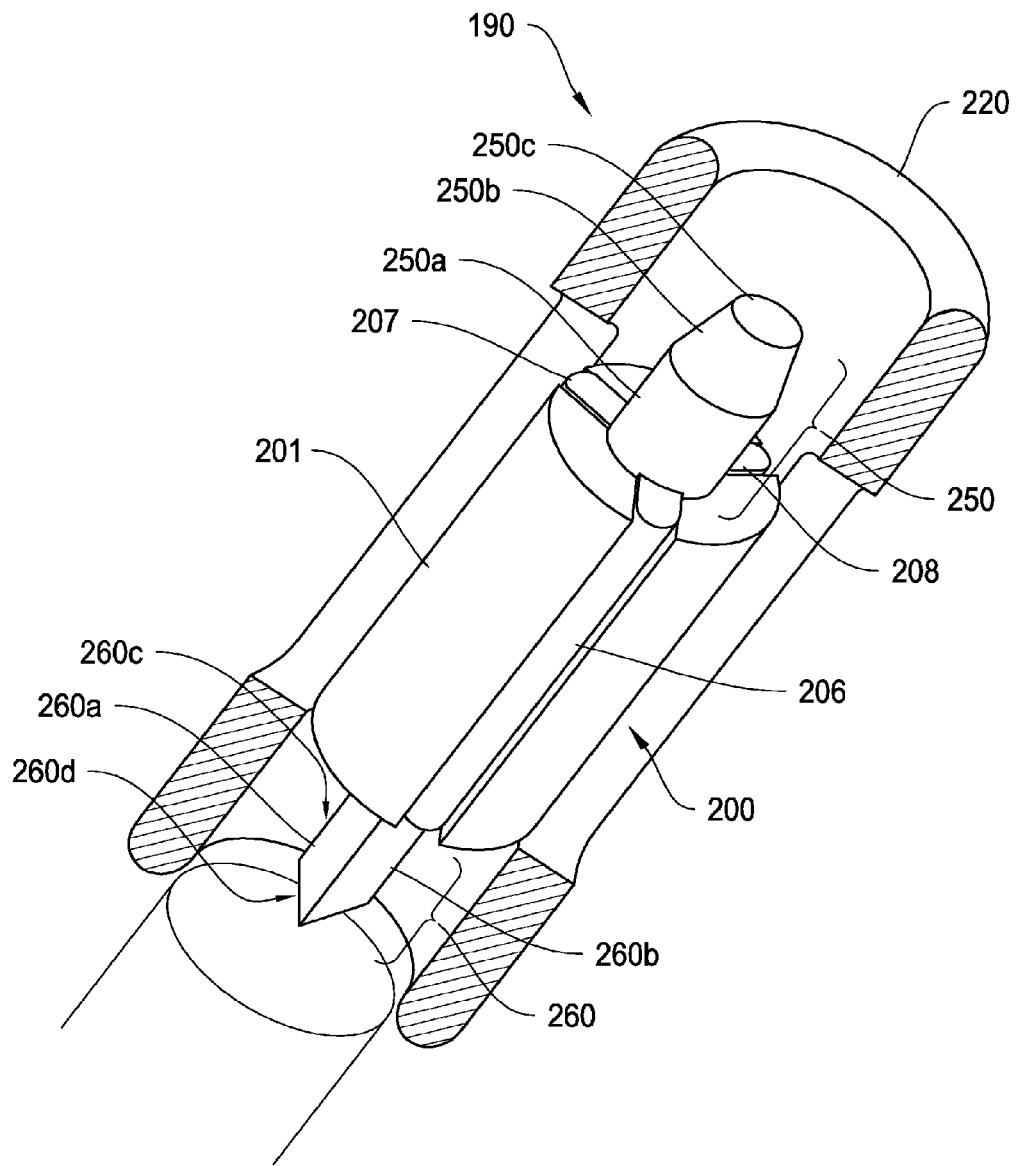
FIG. 9 depicts a cut-away view of the structure of FIG. 8 from outside the shell.

FIG. 9 illustrates a cut-away view of the implant structure 190, with half of the sleeve 220 removed. Shown inside is the strut system 200 having a plurality of wings 206, 207 and 208, and packed about with a biodegradable porous putty or bio-degradable resin 201, similar to putty 101 and wrap 95 disclosed above. As shown, the strut system 200 includes proximal 250 and distal 260 plugs that are used as alternatives to the tips 83 and 85 of the long wings of the implant 140 (shown above). Proximal plug 250 includes a cylindrical base 250a, a blunt tip 250c, and a conical section 250b disposed between the cylindrical base and tip. The base 250a extends from and interfaces with the strut wings 206, 207, and 208 on the end of the strut. The proximal plug 250 is pressed into a cylindrical hole that is bored into the face 97 of the proximal bone segment 102a. On the distal end of the implant 200, a distal plug 260 is formed as a three-sided triangular piece having sides 260a, 260b, 260c, and having a blunt distal face 260d. The plug 260 is pressed into a correspondingly shaped hole, bored as a triangle, into the face 98 of distal bone segment 102b. The plug may also be slip-fitted into the bone. In one advantage, the plug 250 has a different shape than plug 260, which provides additional rigidity and strength to the implant, further assisting in stabilizing it with regarding to axial movement, further reducing the likelihood of slippage within the intramedullary canal and helping further secure the implant in place.

The struts can also be canulated, for example with a central hub similar to hub 90 (see FIGS. 22A-22B) to allow blood or fluid to move longitudinally through the strut. Canals or other channels can also be formed within the strut or on one or more wings of the strut to provide a pathway for blood to flow and cells to grow. For example, one or more canals can be formed within the wings 104-107 of the strut, or within other struts disclosed herein. Channels and canals may also be formed within the scaffolding material, as discussed herein.

Figure 10:
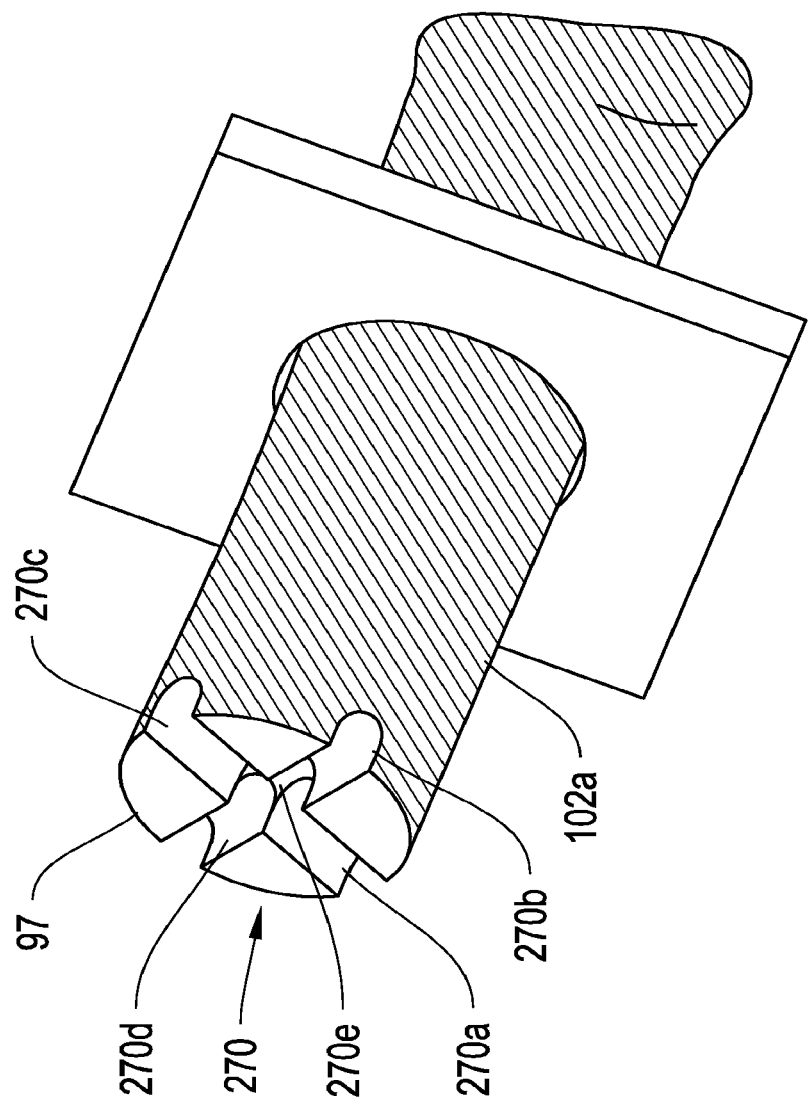
FIG. 10 depicts an example of a slot in a face of a bone segment.

FIG. 10 depicts an alternative embodiment of a slot 270 formed into the proximal face 97 of the bone segment 102a. The depicted slot 270 is in the form of a "+", having four channels 270a, 270b, 270c, and 270d and a center hub receptacle 270e. The slot 270 is sized and shaped to receive a corresponding head from an implant, such as a strut, having a head with a center hub that fits within the receptacle 270e and four wings that fit within the channels 270a-270d.

FIGS. 11A-11C illustrate an alternative version of a sleeve 320, similar to the cylindrical sleeve 120 described above, but having a tapered or sloped transverse arrangement. As shown, the sleeve 320 has a proximal end 320a and a distal end 320b, but the cross-sectional dimension 321 of the end 320b is smaller than the cross-sectional dimension 323 of the end 320a, providing a tapered structure from one end to the other. This tapered structure may be used to more snuggly fit with the bone. FIG. 11C also illustrates the presence of holes 350a and 350b in the sleeve through which a screw or other fastener can be inserted, for fastening the sleeve to the bone inside, to further support the bone. A tapered ellipse or tapered D-shaped sleeve may be used for even better fit.

Alternative shell implementations are also envisioned. As indicated above, biocompatible wraps and sleeves can be used to provide an exterior support for a treated bone. In certain embodiments a wrap is applied to the bone as a sleeve and then changes its physical state to become a hard, biocompatible shell. FIGS. 12A-22B illustrate implementations of such structures. FIG. 12A is a biocompatible wrap material 400 that is used to wrap about a segmented bone or other fracture. The wrap 400 has a plurality of layers of material. The layer 404 is a formable, degradable sheet and has a settable resin layer 402 injected or disposed on its upper surface 405. The resin 402 can include one or more of the resins described above. In use, the resin 402 is disposed on the sheet 404 to form the wrap 400, which is then applied to the bone. It can be wrapped substantially around the bone (270 degrees or more), or preferably completely and may overlap at least once. The wrap is then held in position until the resin has solidified. The materials used for the wrap are pliable and configurable, such that by hand application to the bone they are configured into an implantable sleeve. In certain embodiments, the layer 404 includes polycaprylactone, either alone or in combination with other materials. Other formable polymer materials may also be used.

The materials for the wrap also allow the wrap to be formed and molded initially so that it can conform to the contours of the set bone, forming a sleeve that contours to the bone about its circumference to hold in its reduction configuration. After the sleeve is formed about the bone, the materials change their physical state to become a hard, biocompatible shell sufficient to support the load on the orthopedic bone itself. In certain implementations as discussed further below, the sheet 404 is degradable and the settable resin 402 is hardenable and curable. Thus, after application to the patient's bone, the outer sheet layer 404 degrades and the inner resin layer 402 solidifies, forming a stable shell with contouring suitable to the bone being treated. The degradation rate of the sheet 404 can be controlled by type of material and thickness.

Dimensions for the sheet may include sheets with thickness of about 0.005 to about 0.020 inches, while in certain implementations, the thickness is about 0.01 inches, or about 0.08 to about 0.15 inches. The external dimensions of the wrap 400 are adjusted according to the dimensions needed to treat the bone. Examples include a 6"×5" sheet.

In certain applications, the wrap constructed according to FIGS. 12A-12B provides a strong extra-osseous structure with a high moment of inertia as compared to a plate, nail or other conventional products and, because of its formability, it can be applied to any diameter size bone having any shape or sizing. Because the wrap is wrapped to the bone and because of the change in state of the wrap (e.g., by degradation of the exterior sheet and the solidification of the interior sheet) the sleeve can be applied to the bone without the need for fasteners to fixate it to the bone. The wrap thereby creates a "line-to-line fit" of the wrap and the bone for a more secure and stable connection for treatment. The resin may also include adhesive properties that improve the connection and the interfit between the bone and the wrap.

FIGS. 13A-13C and FIGS. 14A-14F illustrate in further detail application of a wrap 400 similar to the wraps described above. FIG. 13A shows a human bone 410 having a fracture 412 where both ends of the bone 410a and 410b have undergone reduction to an appropriate configuration to allow the bone fracture to begin healing. The reduced bone 410 is laid longitudinally along the upper face of the wrap 400. As shown in FIG. 13B, the left side 404*a* and the right side 404*b* of the lower layer 404 are then folded angularly around the bone to cover most (and preferably all) of the fracture site 412. As shown, a gap 408 is left between the left and right sides 404*a* and 404*b* of the sheet; however, in preferred implementations, the ends of the wrap 400 would extend across themselves without leaving a gap 408. Wrapping the sheet 404 around the bone thus contacts the circumference of the bone 410 with the inner resin layer 402. As shown in FIG. 13C after a period of time, the exterior sheet 404 degrades away and the interior resin layer 402 hardens into a rigid, load-bearing casing 402 that is wrapped in place around the bone and fracture site.

The wrap 400 can also be applied to a more serious fracture, such as a segment defect with a missing bone piece, using a strut to fill the gap of the missing bone. For example, if the bone segments 410*a* and 410*b* were completely segmented with a bone gap similar to segments 102*a* and 102*b* of FIG. 1, any of the struts described herein can be applied to fixate the reduced bone segment 410*a* and 410*b* prior to the application of the wrap. The wrap would then be applied to the exterior circumferential surface of the bone as described above, with the wrap securing the bone ends and the strut in a single support structure. In certain implementations, the wrap and strut are formed and applied as a unitary piece. For example, an intramedullary strut similar to those described above is placed upon the wrap 400 and optionally co-molded with the wrap before the bone is applied, then the bone is applied about the strut similar to the techniques described above, to secure the bone segment ends 410*a* and 410*b* about the strut. After securing the bone ends together, or about the strut, the wrap 400 is wrapped around the bone circumferentially to encircle the fracture site 412, including the bone segment and, the strut (if used).

FIGS. 14A-14F depict a more detailed embodiment of a process for applying a wrap, from a cross-sectional view. As shown, the resin layer 402 and the sheet layer 404 are placed on the surface of the bone 410 (on the far surface) and then, as shown in FIG. 14B, the left ends 400*a* and the right ends 400*b* are raised radially and wrapped around the circumference of the bone 410, leaving a gap 408 (or preferably closing that gap completely). The resin layer 402 thus contacts the circumferential surface of the bone 410, while the sheet 404 is disposed about the layer 402. After a period of time, as shown in FIG. 14B, the sheet layer 404 begins to degrade into partially degraded component 404*x*, while the inter resin layer 402 solidifies. FIG. 14E depicts further degradation of layer 404*x* until it is no longer present by the time the resin is completely set, as shown in FIG. 14F.

Figure 15A:
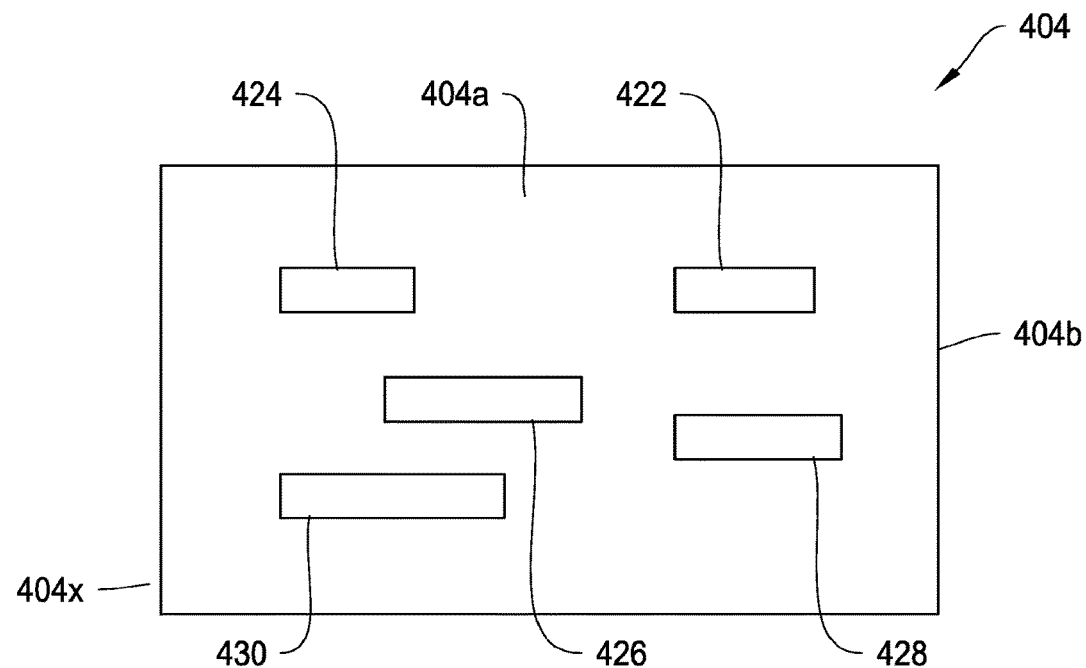
FIGS. 15A-15D depict a process for preparing a fracture support sleeve from a wrap, having windows disposed within the sleeve.
Figure 15B:
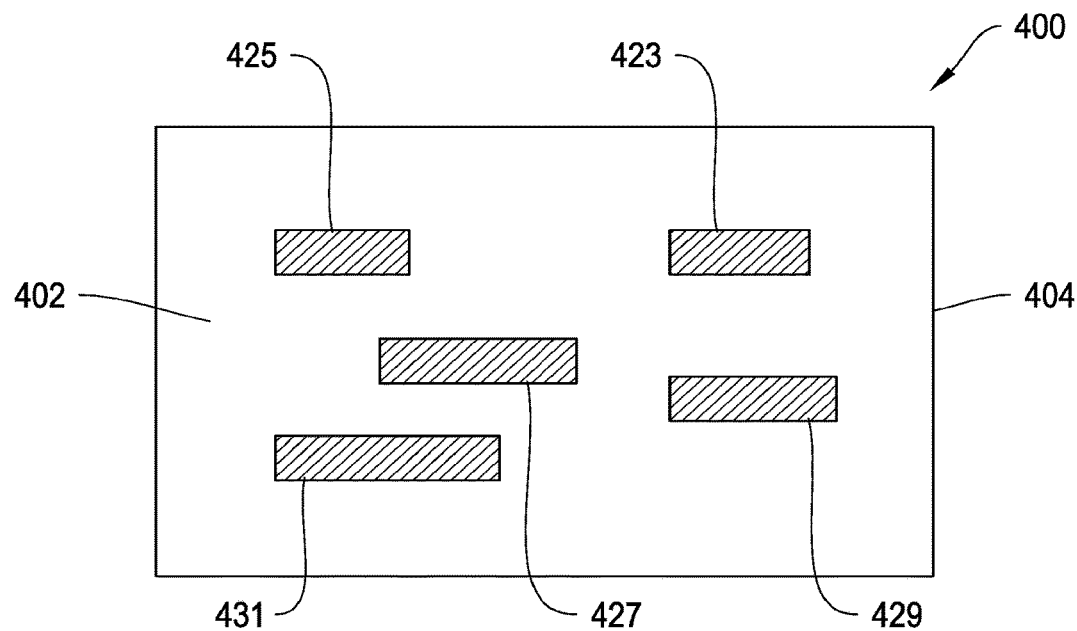
Figure 15C:
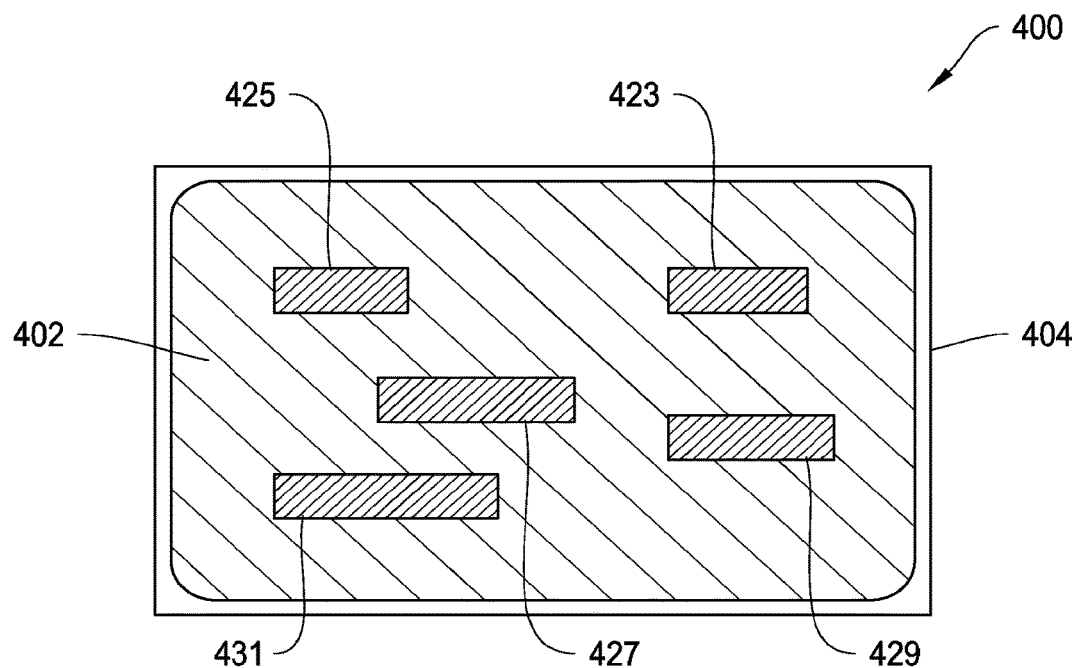
Figure 15D:
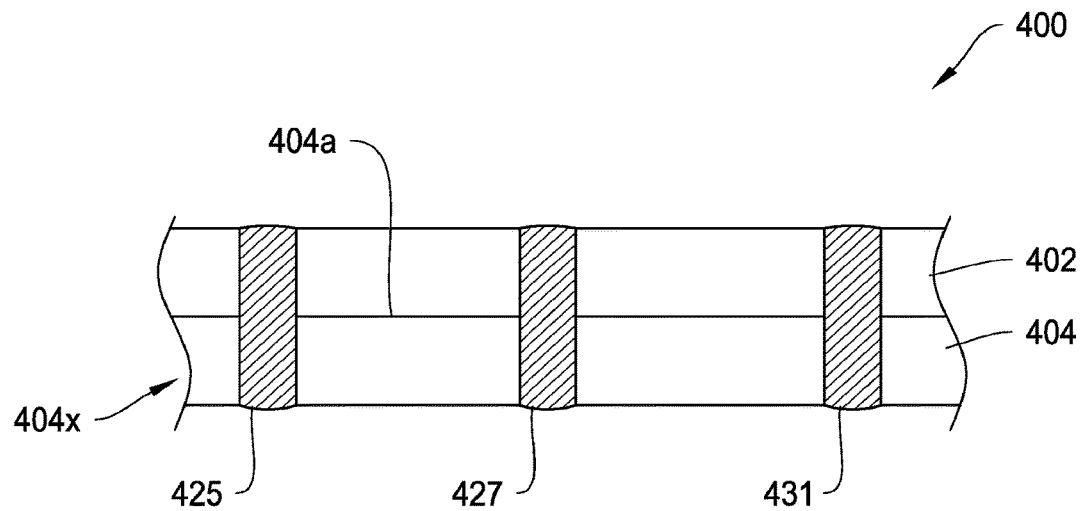

The wrap can be modified to provide one or more windows or flow pathways, similar to embodiments described above. For example, FIGS. 15A-15D depict a process for implementing window structures within the wrap 400 prior to its application to the bone, so that these structures are in place after solidification to allow blood flow from the exterior of the shell into the bone during healing. As shown, FIG. 15A depicts the lower sheet layer 404 having a series of windows 422-428 placed upon its upper surface. FIG. 15B shows a set of biocompatible foam portions 423-431 disposed respectively upon the windows of FIG. 15A. After disposition of the foam, the surgeon or manufacturer applies the upper resin layer 402 to the top surface 404 of the sheet. The resin 402 is disposed by injection or by hand pressing or other suitable approach and is distributed about the surface of the upper face 404 so that it surrounds the foam portions 423-431. FIG. 15C depicts a top view of the resin 402 distributed about the windows 423-431 on the top surface 404 of the lower sheet 404. FIG. 15D shows a cross sectional view of the wrap 400 from the left side view 404 (which is the distal end of the wrap). As shown, windows 425, 427 and 431 protrude across the surface of the wrap 400, allowing fluid such as blood or interstitial fluid to pass from the bone to the exterior of the splint 400 and back. This allows for enhanced nourishment of the bone during its healing process.

As with the windows in sleeves described above, the windows 422-428 are sized, shaped and positioned based upon at least two factors. One factor is the desire to provide as large of an opening as possible to allow vascular flow in and out of the wrap and into contact with the bone to facilitate healing. The second factor is to ensure that the opening doesn't compromise the strength of the implant to support the bone and reduce stresses around the bone where possible. The size and location of the windows would be determined to meet the particular patient's need.

FIGS. 16A and 16B depict a dual-layer wrap material 430, with similar components and materials as wrap 400 but with an alternative configuration for the settable resin. As shown, the resin layer 432 is disposed upon the upper surface of the sheet 404 in a series of separated resin packets 440*a*-440*d*. As shown, the resin packets 440*a*-440*d* are spaced apart from each other on the upper surface 404*a* of the sheet 404. Spacing portions 441 extend between each of the packets 440*a*-440*d* to provide spacing, leaving a number of gaps. To prepare this structure 430, the technician or surgeon lays a sheet 404 on a support surface and then applies the packets 440*a*-440*d* upon the surfaces at pre-determined locations or at a random locations, as preferred. One or more additional connecting sections 443*a*-443*d* are provided to inter-connect two or more of the various packets, which may be interconnected to form a fully unitary piece. In certain implementations, multiple pieces are included, whereas in other embodiments the packets are unitarily connected through the sections 443*a*-443*d* in the resin layer 432. In use, after the resin packets are placed upon the sheet 404, the wrap 430 is applied about the bone of the patient similar to the methods described above. After application, the lower sheet 404 degrades and the upper resin 432 solidifies to form a hardened, load bearing structure to support the fracture site.

Figure 17:
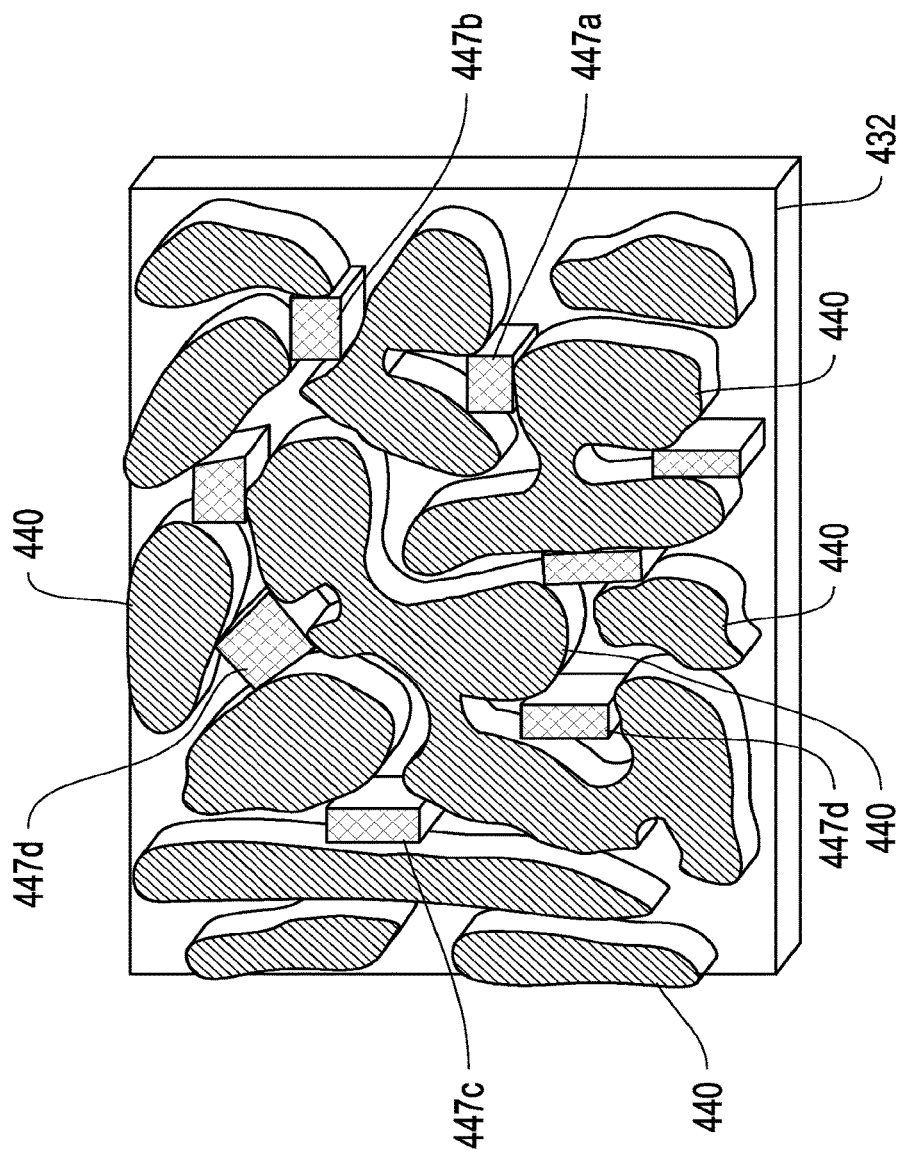
FIG. 17 depicts an implementation of the structure of FIGS. 16A-16B having foam windows disposed between packets of settable resin on the sheet.

FIG. 17 depicts an alternative implementation of the structure of FIG. 16A, having one or more foam windows 447*a*-447*d* disposed between the packets 440. The foam windows 447*a*-447*d* are placed upon the lower sheet 404 and then the resin packets 440 are placed upon the sheet about the windows 447, thereby providing the wrap 430 with spacings between the support packets and windows that permit and control the flow of fluid from the exterior to the interior of the wrap to contact the fracture site.

Figure 18B:
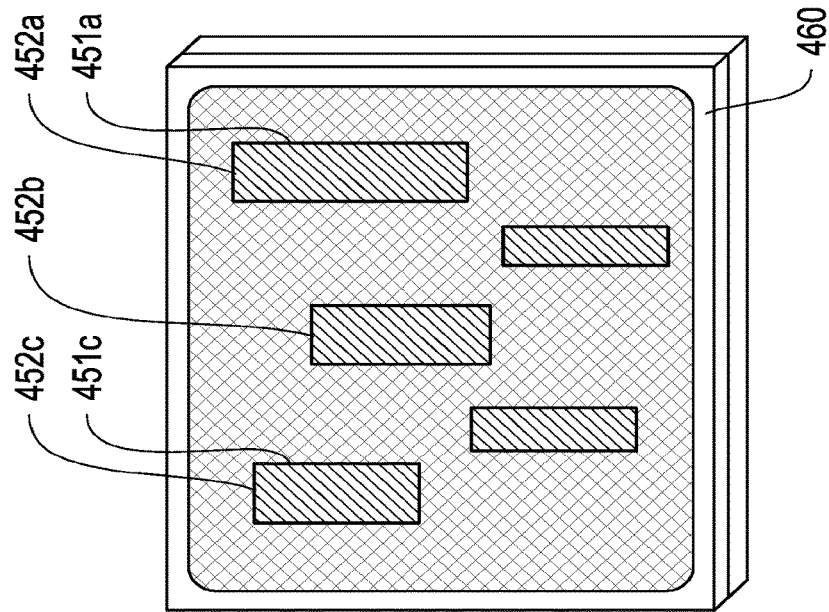
FIGS. 18A-18B illustrate an embodiment that applies foam windows to the wrap.
Figure 18A:
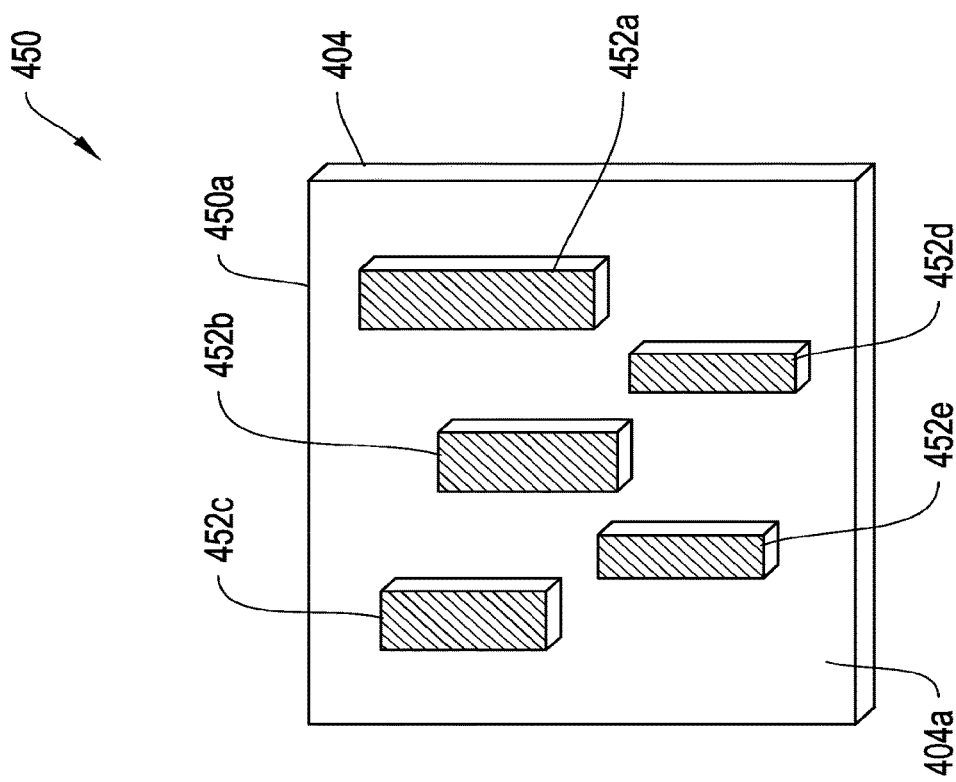

In certain implementations the foam window dimensions can be adjusted to enhance or restrict blood flow and interstitial fluid flow. FIGS. 18A-19B provide an embodiment that applies foam windows, similar to those described above, at different heights and dimensions. FIG. 18A shows wrap 450 having a lower sheet layer 404 and strips of foam 452*a*-452*e* disposed on the upper surface 404*a* of the lower sheet. FIG. 18B depicts an upper resin layer 460 disposed on the upper surface 404*a*, extending about the foam windows 452*a*-452*e* to provide a bone contact layer. The resin layer 460 is applied to the upper surface 404*a* so it surrounds and abuts the edges 451 of the foam strips 452. As shown, for example, resin 460 abuts edge 451*c* of the foam strip 452*c*. FIGS. 19A-19B provide cross-sectional views of the structure of FIGS. 18A-18B, where foam strips 452*a*-452*c* extend higher than the height of resin layer 460. In particular, as shown, the foam strips are higher by a distance 'X' above the upper surface 460a of the resin layer 460. This higher foam strip can provide a more secure and stable contact between the bone and the exterior portion of the wrap, to further support the bone and facilitate blood flow.

Figure 20:
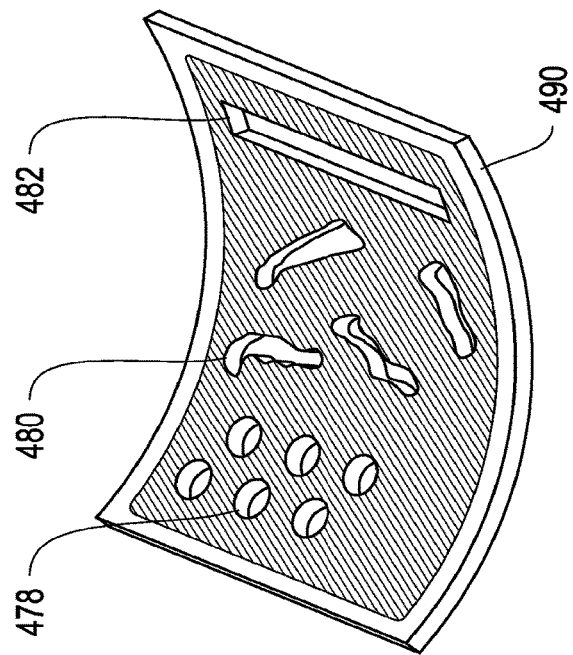
FIG. 20 illustrates features provided for enhanced surface contact.

In certain implementations, adhesive properties are configured in the inner surface 490 of a biocompatible sleeve (e.g., sleeve 120) to improve the surface contact between the resin or other filler material and the sleeve, thereby helping to enhance the stability of the implant for supporting the fracture. Examples of such properties may include channels, recesses, grooves, dimples, knurls or other structural mechanical features added to the sleeve, which enhance surface contact and connection between the sleeve 120 and the patient's bone. FIG. 20 depicts examples of such structures, including dimples 478, recesses 480 and channels 482, each formed within the interior surface 490 of the sleeve. As will be appreciated, sleeves formed from the wrap-like structures disclosed above can also be enhanced by the injection of resin or other materials to fill in other gaps that exist between the interior portion of the wrap, such as wrap 400 or wrap 450, similar to the injection process described above, for example FIG. 7E-7F. In such cases, the inner surface features 478-482 can be filled with resin, putty or other filler material to provide enhanced surface contacting and adhesion between the sleeve and the resin, for example wrap 400 or wrap 450, for enhanced fixation.

Although not shown, sleeves prepared by use of a wrap embodiment can also be structured to accommodate screw holes to receive fasteners (either in locking or non-locked-type) to provide supplemental fixation to anchor the sleeve to the bone. Applying fastener holds creates a circular external fixator. The fasteners used can be locking screws or non-locking screws. For example, locking structures, such as those disclosed in U.S. patent application Ser. No. 11/966,795 ("Systems and Methods for Using Polyaxial Plates"), or those in U.S. patent application Ser. No. 12/069,331 ("Systems and Methods for Using Polyaxial Plates") may be used to lock the sleeve to the bone to enhance the fixation or, if desired, to avoid having to inject putty into the sleeve space. As noted above, such items are not required, but may be used in certain embodiments where desired. The apertures could be provided in the sleeve, or could be created and applied in a position the user desires prior to apply the wrap to the bone.

Figure 21:
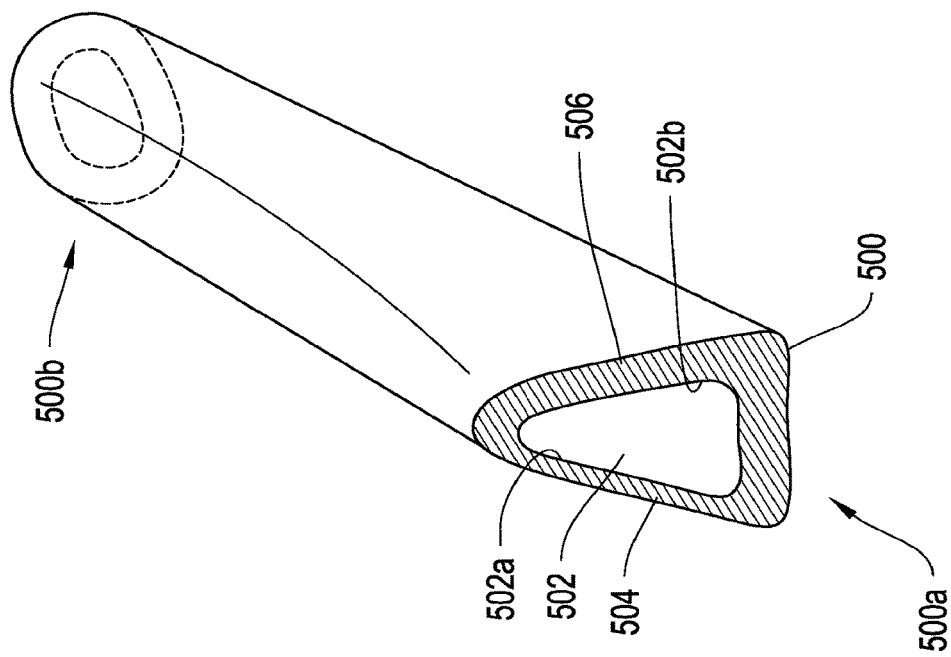
FIG. 21 depicts a sleeve disposed about a tibial bone having anterior and posterior contact surfaces.

In certain implementations, the sleeve is designed to closely fit with the bone according to the unique shapes of the bone being treated. The sleeve can also be designed with portions of different thickness to align with regions on the bone that are subject to different stresses. For example, this sleeve can be designed with portions that are thicker in regions where high stresses will be experienced, and thinner in regions where lower stresses will be present. As depicted in FIG. 21, the design of the wrap-based sleeves with variable thickness allows for a bone-specific profile. For example, some bones, such as the tibia, have portions that are non-cylindrical, and therefore a sleeve formed by the hand-wrap process as described above (and other sleeves disclosed herein, also) may take an oval, triangular, or other non-symmetric shape. In FIG. 21, a wrap 500 is disposed about a tibial bone 502, the wrap 500 having a first end 500a and a second end 500b, which correspond to respective proximal and distal regions of the tibia. The wrap 500 also has anterior and posterior regions that are shaped to fit the anterior and posterior regions 502a and 502b of the bone 502. More particularly, the wrap 500 has a thin portion 504 applied in a thin layer along the anterior, flat surface 502a of the tibia 502 and a relatively thick portion 506 configured to fit about the posterior portion 502b of the tibia 502. Because the shin area (502a of the tibia) has a relatively thin layer of skin protecting it, with little muscle or tissue between the skin and the bone, the use of a thick wrap under the skin would be bulky and unattractive and potentially impair the treatment protocol for the patient, for example as it might allow the wrap to bulge the skin in a painful or cumbersome or unattractive way. Therefore, the anterior portion of the wrap is provided by a relatively thin layer 504. In contrast, the posterior portion of the tibia 502b has a thicker portion of bone and is surrounded by a thicker layer of muscle and other tissue, thus the posterior portion 506 of the wrap is thicker than the anterior portion 504, for a more customized and aesthetic fit and more mechanical support for bone loads.

The wrap 500 is also configured to vary longitudinally along the bone 502. Also shown in FIG. 21, the first end 500a of the wrap 500 corresponds to a proximal region of the tibia, which has a first cross-sectional shape, and the second end 500b corresponds to a distal region of the tibia which has a second cross-sectional shape that is different than the first shape. The first end 500a has a first cross-sectional shape (e.g., a triangle), which corresponds to the cross-sectional shape of the bone in the proximal region of the bone, while the second end 500b has a second cross-sectional shape (e.g., an oval) to correspond to the cross-sectional shape of the bone in the distal region. It will be appreciated that other sleeves disclosed herein may also be structured with cross-sectional shapes that vary from one portion of the sleeve to another. For example, D-shaped, O-shaped, C-shaped, or other shapes could be used on one end of a sleeve, while the same or alternative shapes may be used on another end of the sleeve. The cross sectional shape of the sleeve, and accordingly the fit to the bone, can be determined by the technician or by the surgeon, as needed to fit the particular bone being treated. The profile of the wrap can thereby be selected to optimize patient comfort, wearability, support and strength.

Alternative implementations of the strut 100 are also envisaged. Examples of alternative strut structures are included in FIGS. 22A-22B. These are intended to be, as with other embodiments disclosed herein, illustrative only and non limiting. One of skill in the art will appreciate potential variations and alternatives by reference to these and the other figures and embodiments. FIGS. 22A-22B depict top and side views of an alternative implementation of a strut 500 having wings 404, 405, 406, and 507, similar to the embodiments described above. As noted above, the wings are disposed about a central hub or axis 90, which extends longitudinally through the strut 500. In the implementation shown in FIGS. 12A-12B, the central hub 90 is structured as a through-passage or flow tube 92 extending longitudinally through the strut 500 from hub end 90A to hub end 90B. The flow tube 92 is molded into the strut 500, and the thin, molded degradable polymer walls 402 and 404 surround the tube 92 and join the wings 404, 405, 406, and 507 around the central hub 90.

Figure 23:
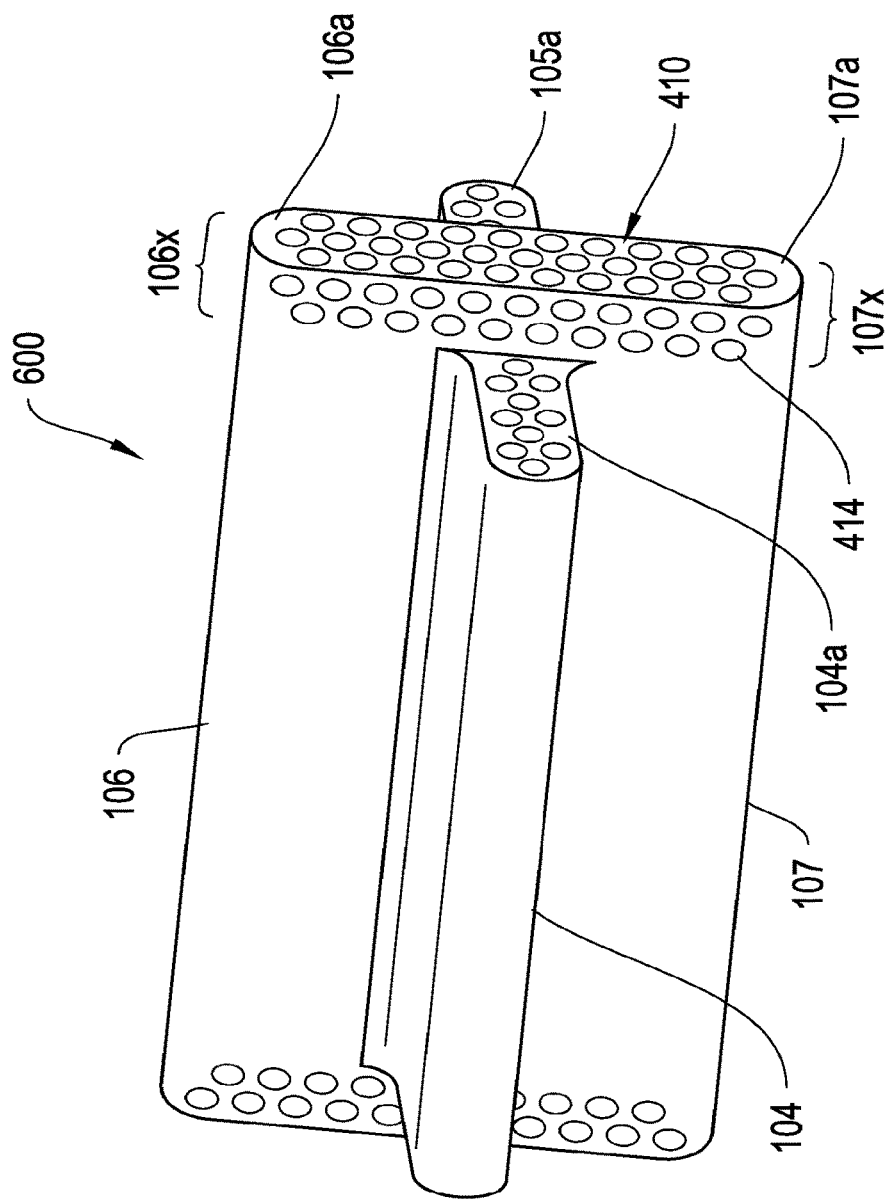
FIG. 23 depicts an embodiment of an intramedullary strut.

FIG. 23 depicts an alternative implementation of an intramedullary strut 600, similar to the strut 100 described above, but having dimpled indentations applied to surfaces on the proximal and distal ends of the strut that will interface with the bone segments. As shown, the proximal end 400 of the strut 600 contains a plurality of dimples 410 disposed along the bone contacting surfaces 404, 405, 406, and 407. Additional dimpling can be applied along the shafts of the wings. For example, dimpling 414 is disposed along the shaft portions 406X and 407X which are portions of the wings that will be fitted within slot 93 on the bone segments 402, as described above. The dimpling (or other similar holes or intrusions), also provide additional surface area with respect to which new bone material can grow during revascularization and healing, thereby further securing the implant in place and facilitating further strengthening of the healing of the wound.

Figure 24:
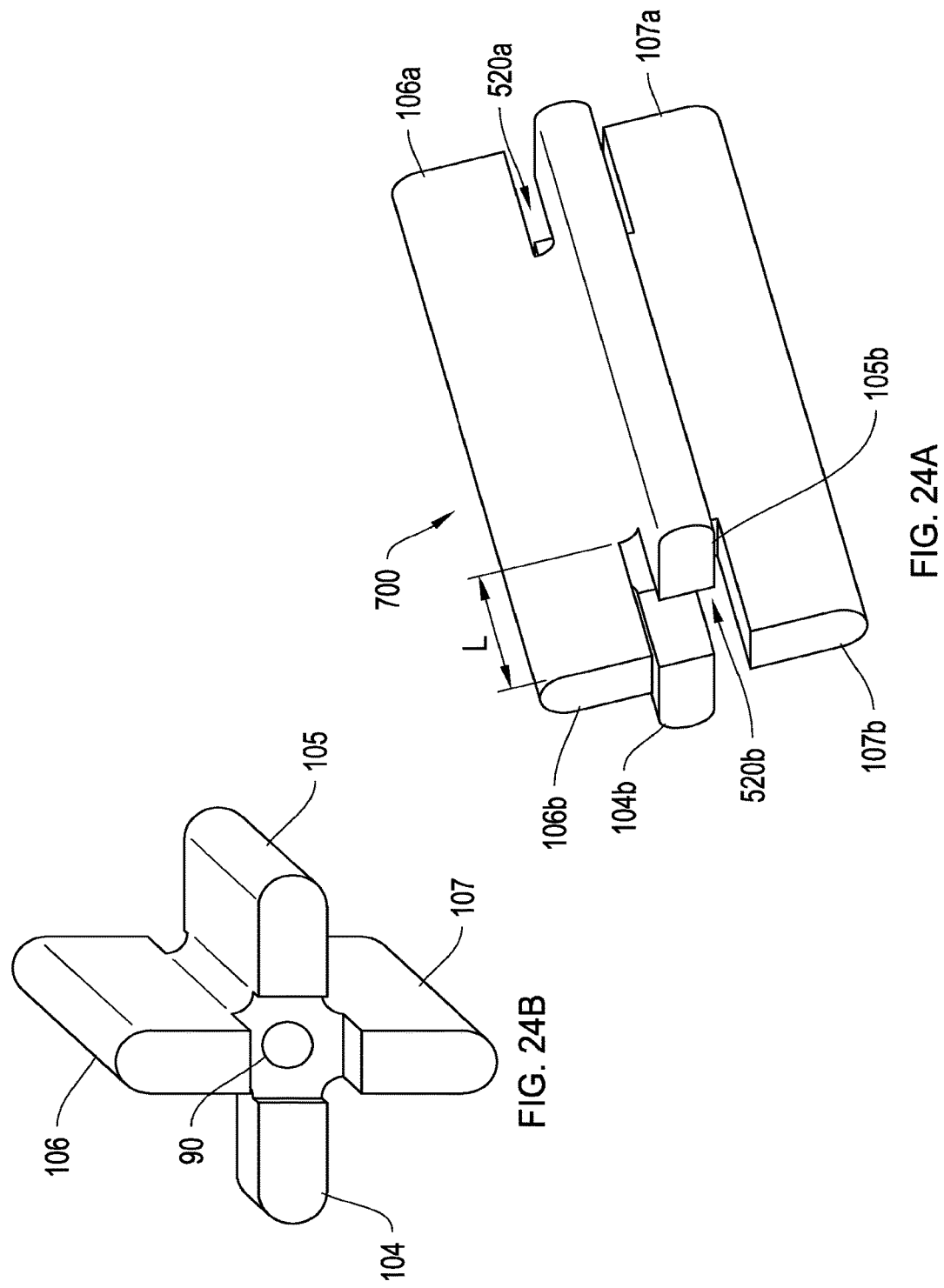
FIGS. 24A-24B depict side and top views of an embodiment of an intramedullary strut.

FIGS. 24A-24B depict an additional alternative implementation of a intramedullary strut 700, similar to the struts described above, but having proximal and distal ends 100a and 100b structured with extending wing tips that protrude into individual slots bored or carved into the opposing segment faces of the bone 402. In particular, as shown in FIG. 14A, the distal ends 404, 405, 406, and 407 of the strut 700, have a large open space 502b bored within them to separate the tips from each other along length L of the distal end of the strut 700. A corresponding opening 520a is optionally disposed on the proximal end. In this configuration, the distal and proximal end segments of the wings of the strut 700 are individually disposed within corresponding individual slots bored into the faces of the segments (i.e., segments 402 and 402), such that the interfaces 97 and 98 of the bone segments and the strut wing tips each include or a plurality of (or in this case four) separate tips that can individually strengthen the connection between the bone and strut.

As one of skill in the art will appreciate, any of the putties, wraps, sleeves, foams, and central hubs or alternatives thereof, as described above, could be implemented with any of these alternative versions of the struts 100, 500, 600 and 700. Any of the implants, methods, systems and devices disclosed herein may include one or more internal or external fixation devices to further anchor a sleeve to a patient's bone. One of the skill and art will also recognize other possible variations.

Any of the devices, systems, implants, and methods may also incorporate bioactive molecules that promote beneficial processes, such as healing, regeneration, bone regrowth and mineralization, and discourage undesirable processes, such as infection or inflammation. The bioactive molecules may be incorporated, for example, into the foam, wrap, putty, resin or other components of the implants. The molecules may include, but are not limited to, antibiotics; growth factors, including, but not limited to, insulin-like growth factors (IGF-I & II), transforming growth factors (TGFbs 1-3), fibroblast growth factors acidic and basic (aFGF & bFGF), platelet derived growth factor (PDGF), and bone morphogenetic proteins (BMPs); interleukins (IL), such as IL-1 b, IL-3 (Multi CSF), IL-4, IL-6, and IL-8; tumor necrosis factors TNF alpha and TNF beta; interferons (IFNs); colony stimulating factors; hormones, including but not limited to steroids, such as estrogen, and peptide hormones; anti-inflammatory molecules, including non-steroidal anti-inflammatory molecules; or any combination or variation thereof. The bioactive molecules may be incorporated into the implants, devices or components according to any suitable method, including but not limited to, caging, impregnation, complexing, or chemical bonding, including the use of covalent and non-covalent bonds. Examples of beneficial modification with biologically active molecules include modification GRGD (Gly-Arg-Gly-Asp) peptide sequence to encourage host cell attachment and migration, and encapsulation of growth factors, such as TGF-1, which acts to direct cell migration and differentiation.

Figure 25:
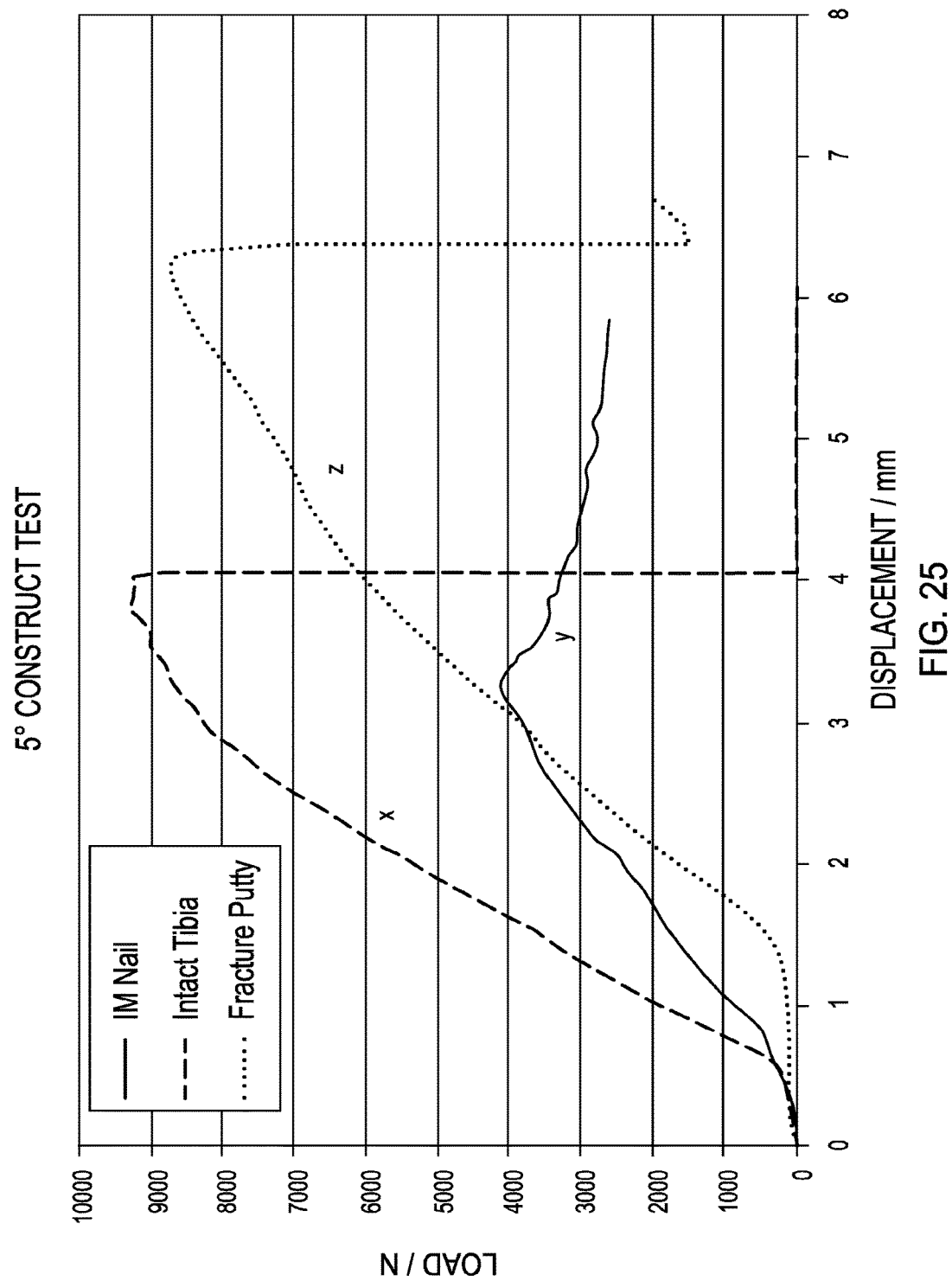
FIG. 25 depicts data from a Construct Test performed on a fractured tibia repaired with a surgical system according to teachings disclosed herein.
Figure 26:
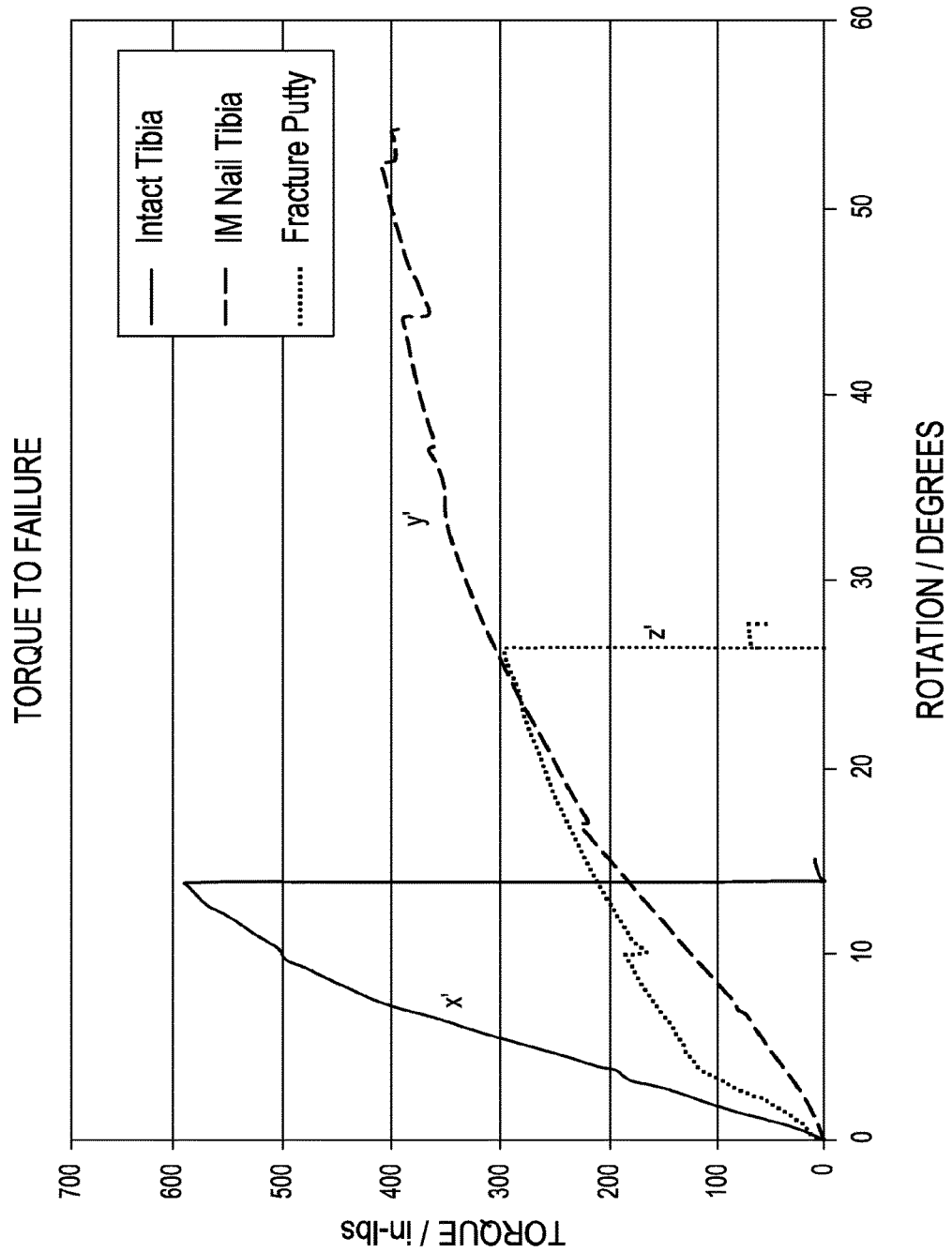
FIG. 26 depicts data from a Torque-to-Failure Test performed on a fractured tibia repaired with a surgical system according to teachings disclosed herein.

The data of FIGS. 25-26 illustrate the results of tests performed on three sets of bone construct samples. A first sample set included a fractured tibia that was repaired using a surgical system having an intramedullary implant and a sleeve, similar to the implant 140 described above. For that set, an implant 440 and sleeve 420 were prepared and installed in a bone containing a mid-diaphysis segmental defect, according to the procedure described in FIGS. 7A-7F. A second sample set included a fractured tibia repaired using a typical IM nail. A third sample set included an intact tibia.

FIG. 25 illustrates the results of a 5° Construct Test to test the stiffness of the various bone constructs. In this test, the tibia was mounted vertically in the ML plane and 5° away from vertical in the AP plane, in order to simulate the loading of the tibia at the point of greatest load. The tested constructs were each aligned and bolted between two pressure plates. The pressure plates were compressed against each other under a load to test the bending strength and stiffness of the repaired bone. The force applied to the plates was increased (i.e., the load was increased) and displacement measured.

The data shown in FIG. 25 illustrate the displacement of the various tested bones as a function of the load applied, as reflected in the curves x, y, and z. The slope of each curve is indicative of stiffness and bending strength of the respective bone construct. The displacement (or bending) of the intact tibia is shown in curve "x". It displaced approximately 4 mm until it fractured under a load of about 9000N. The displacement of the bone repaired using the conventional IM nail varied according to the load applied as shown in curve "y". It displaced approximately 3 mm before it broke under a load of about 4000N. The bone repaired using the fracture system with the repair system described in FIGS. 7A-7F showed significantly increased strength, compared to the IM Nail repaired system. Its displacement varied according to load as shown in curve "z". As shown, the repaired bone with curve z did not break until the load reached approximately 9000N. The slope of the curve is similar to the slope of curve x, illustrating that the support provided by the surgical system with the strut described above provided similar strength and resistance against bending and axial forces to that of an unbroken bone. The point of failure was much higher than that of the IM Nail repaired bones, illustrating that the bone repaired according to the procedure of FIGS. 7A-7F had greater strength and stiffness.

FIG. 26 illustrates the results of a Torque to Failure test applied to bone constructs treated similarly to those tested and illustrated in FIG. 25—intact tibia, IM Nail repaired tibia, and fractured tibia repaired by the procedure of FIGS. 7A-7F. For this test, torque was applied to each bone, and the rotation of the bones was measured in degrees, as resulting from the applied torque. The bones were torqued until they failed. The slopes of the curves x', y' and z' are indicative of torsional stiffness of the bones. As shown, the slope or stiffness of the structure repaired according to the procedure of FIGS. 7A-7F had a slope and torsional stiffness (curve z') that was similar to that of the IM Nail repaired bone (curve y'), but a lower slope (and a lower stiffness) than the intact tibia (curve x'). This illustrates that the tibia repaired according to FIGS. 7A-7F had a comparable torsional stiffness to the traditional IM Nail repaired bone.

Figure 27:
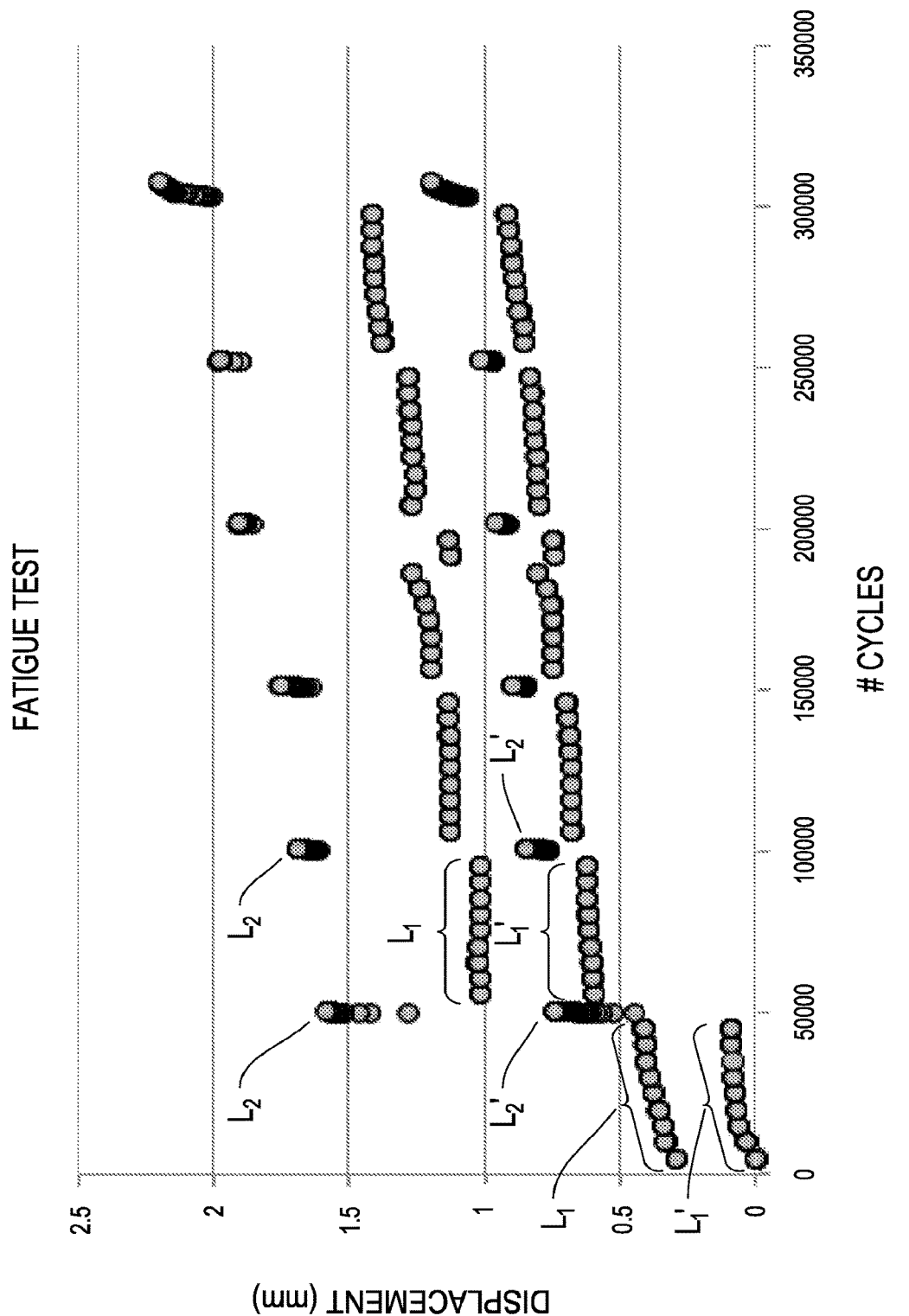
FIG. 27 depicts data from a Fatigue Test performed on a repaired fractured bone.

FIG. 27 shows the results of a fatigue test applied to a fractured bone repaired with a strut and sleeve combination, according to embodiments disclosed herein. The repaired bone was oriented in 5° construct test, a according to a similar protocol of FIG. 26, to test the capacity of the bone to support loading. Samples of the repaired bone were cyclically loaded to simulate loading conditions during normal activities, such as walking and standing. Biphasic loading of 1,100N and 2,200N was applied cyclically for 303,000 cycles (pattern of 50,000 cycles at 1,100N followed by 500 cycles at 2,200N). The number of cycles and variation in the loads applied were designed to simulate normal activities performed over a 3 month period. The results can be seen in FIG. 27. As shown, during the first 50,000 cycles, loads of 1100 N ($L_1$) and 110 N ($L_1'$) were applied, cyclically back and forth to the bone for approximately 50,000 cycles, to simulate normal walking. The two loads were then doubled to 2200 N ($L_2$) and 220 N ($L_2'$) for a few hundred cycles to simulate a periodic enhanced load, as may occur, for example, when a person jumps or trips. The repaired bone displaced very little during the first 50,000 cycles, with displacement at high load 1100 N ($L_1$) remaining under 0.5 mm, and displacement of only 1.5 mm during application of the second load 2200 N ($L_2$). The loading pattern was then repeated by applying the original loads 1100 N ($L_1$) and 110 N ($L_1'$) over subsequent 50,000 cycles, followed by a repeated short cycle application of the second loads 2200 N ($L_2$) and 220 N ($L_2'$). In that repeated phase, the largest displacement did not reach 2 mm. The loading pattern was repeated four more times, and the largest displacement observed, at approximately 300,000 cycles, was less than 2.5 mm, indicating that over the course of a simulated 3 month period of normal activity the repaired bone showed very little fatigue.

It is to be understood that the forgoing description and examples are merely illustrative and are not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A kit for use in forming an orthopedic fracture repair implant, comprising:
   a first material that is moldable and degradable and has an outer surface and an inner surface; and
   a second material that is positionable to overlie the first material and formable into a curable layer that, upon curing, hardens into a hard shell that is biocompatible with a patient's bone; and
   wherein the first material is a polymer material and the second material is a biocompatible resin.

2. The kit of claim 1, wherein at least one window is defined by the first material.

3. The kit of claim 2, wherein the at least one window includes a transparent portion of the first material.

4. The kit of claim 2, wherein the at least one window provides an opening that extends through the second material.

5. The kit of claim 4, further comprising a foam portion positioned over a surface of the at least one window.

6. The kit of claim 5, wherein the foam is positioned within the at least one window.

7. The kit of claim 4, wherein the second layer comprises a plurality of curable portions spaced apart from each other on the first material.

8. The kit of claim 7, wherein at least a first of the plurality of curable portions extends along a first border of the window and at least a second of the plurality of curable portions extends along a second border of the window.

9. The kit of claim 8, further comprising a foam portion positioned over a surface of the at least one window, and wherein the foam portion is positioned between adjacent ones of the curable portions.

10. The kit of claim 1, further comprising a foam portion, wherein the second material has a first thickness, the foam has a second thickness, and the second thickness is greater than the first thickness.

11. The kit of claim 1, further comprising a chemical catalyst within the second material.

12. The kit of claim 11, wherein the chemical catalyst is included in a concentration within the second material sufficient to catalyze curing of the second material in an exothermic reaction.

13. The kit of claim 12, wherein the chemical catalyst is selected from a tin-based catalyst and a zinc.

14. The kit of claim 1, wherein the first and second materials are each configured as a hand-moldable, pliable flat sheet.

15. The kit of claim 1, wherein the first and second materials are formed in first and second layers, respectively, and together have a width that extends partially but not completely around a circumference of a patient's bone when the first and second layers are rolled into a tube.

16. The kit of claim 1, wherein the first and second materials are formed in first and second layers, respectively, and together have a thickness of between about 1 mm to about 10 mm.

17. The kit of claim 16, wherein the thickness is between about 4 mm to about 5 mm.

18. The kit of claim 1, wherein the first material is polycaprylactone.

19. A kit for use in forming an orthopedic fracture repair implant, comprising:
   a first material that is moldable and degradable and has an outer surface and an inner surface;
   a second material that is positionable to overlie the first material and formable into a curable layer that, upon curing, hardens into a hard shell that is biocompatible with a patient's bone; and
   a stiff polymer strut having first and second ends, with a longitudinal axis and at least one wing radially extending from the longitudinal axis.

20. A kit for use in forming an orthopedic fracture repair implant, comprising:
   a pliable material formed into a sleeve, the sleeve having a formable and degradable first layer and a second layer positioned on the first layer; and
   wherein the second layer is a formable polymer that is curable into a hard shell and biocompatible with a patient's bone, and wherein the second layer comprises a biocompatible resin.

21. The kit of claim 20, wherein at least one window is defined by the first layer.

22. The kit of claim 20, further comprising a chemical catalyst within the formable polymer, wherein the chemical catalyst is included in a concentration within the formable polymer sufficient to catalyze curing of the formable polymer in an exothermic reaction.

23. The kit of claim 22, wherein the chemical catalyst is selected from a tin-based catalyst and a zinc.

24. A kit for use in forming an orthopedic fracture repair implant, comprising:
   a pliable material formed into a sleeve, the sleeve having a formable and degradable first layer and a second layer positioned on the first layer;
   a stiff polymer strut having first and second ends, a longitudinal axis, and at least one wing radially extending away from the longitudinal axis; and
   wherein the second layer is a formable polymer that is curable into a hard shell and biocompatible with a patient's bone.

25. A kit for use in forming an orthopedic fracture repair implant, comprising:
   a first polymeric material configured to be rolled into a sheet, the polymeric material formable into a first layer that is moldable and degradable; and
   a second material that is formable into a curable layer that is configured to overlie the first layer and to harden into a hard shell that is biocompatible with a patient's bone; and
   a strut having a first end and a second end, the strut including one or more wings extending radially away from a longitudinal axis of the strut.

26. The kit of claim 25, wherein at least one window is defined by the first polymeric material.

27. The kit of claim 26, wherein the at least one window provides an opening that extends through the second material.

28. The kit of claim 25, further comprising a chemical catalyst within the second material, wherein the chemical catalyst is included in a concentration within the second material sufficient to catalyze curing of the second material in an exothermic reaction.

29. The kit of claim 28, wherein the chemical catalyst is selected from a tin-based catalyst and a zinc.

30. The kit of claim 25, wherein the first polymeric material is polycaprylactone and the second material is a biocompatible resin.

* * * * *